(12) United States Patent
Walder et al.

(10) Patent No.: US 7,276,337 B2
(45) Date of Patent: *Oct. 2, 2007

(54) COMPOSITIONS AND METHODS FOR VISUAL RIBONUCLEASE DETECTION ASSAYS

(75) Inventors: Joseph Alan Walder, Chicago, IL (US); Mark Aaron Behlke, Coralville, IA (US); Eric Jeffrey Devor, Iowa City, IA (US); Lingyan Huang, Coralville, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 401 days.

This patent is subject to a terminal disclaimer.

(21) Appl. No.: 10/694,480

(22) Filed: Oct. 27, 2003

(65) Prior Publication Data

US 2004/0137479 A1 Jul. 15, 2004

Related U.S. Application Data

(62) Division of application No. 09/968,733, filed on Oct. 1, 2001, now Pat. No. 6,773,885.

(60) Provisional application No. 60/236,640, filed on Sep. 29, 2000.

(51) Int. Cl.
*C12Q 1/68* (2006.01)
*C07H 21/02* (2006.01)
*C07H 21/04* (2006.01)

(52) U.S. Cl. ............ 435/6; 536/23.1; 536/24.3
(58) Field of Classification Search .......... 435/6; 536/23.1, 24.3
See application file for complete search history.

(56) References Cited

U.S. PATENT DOCUMENTS

| | | | | |
|---|---|---|---|---|
| 5,792,615 | A * | 8/1998 | Arnold et al. | 435/6 |
| 6,150,097 | A * | 11/2000 | Tyagi et al. | 435/6 |
| 6,355,421 | B1 * | 3/2002 | Coull et al. | 435/6 |
| 6,444,421 | B1 * | 9/2002 | Chung | 435/6 |
| 6,451,535 | B1 * | 9/2002 | Jenne et al. | 435/6 |
| 2002/0102571 | A1 * | 8/2002 | Theaker et al. | 435/6 |
| 2002/0110823 | A1 * | 8/2002 | Hogan | 435/6 |

FOREIGN PATENT DOCUMENTS

| | | | |
|---|---|---|---|
| WO | WO99/05314 | * | 2/1999 |
| WO | WO 99/47704 | * | 9/1999 |

OTHER PUBLICATIONS

Diamond et al. Methods in Enzymology 100 : 431-453 (1983).*
The Stratagene Catalog , p. 39 (1988).*

* cited by examiner

*Primary Examiner*—Ethan Whisenant
(74) *Attorney, Agent, or Firm*—John A. Petravich

(57) ABSTRACT

The present invention relates to methods for detecting the presence of ribonuclease enzymes, more specifically to methods that provide for a visual detection assay. The methods entail contacting a test sample suspected of containing ribonuclease activity with a substrate containing a ribonuclease-sensitive internucleotide linkage flanked directly or indirectly by a fluorescence reporter group and a dark quencher, such that if a ribonuclease activity is present in the sample, the ribonuclease-sensitive internucleotide linkage is cleaved and the fluorescence reporter group emits a visually detectable signal. The present invention further provides novel nucleic acid compositions used as substrates for such assays and encompasses kits for performing the methods of the invention.

3 Claims, 7 Drawing Sheets

Figure 1:
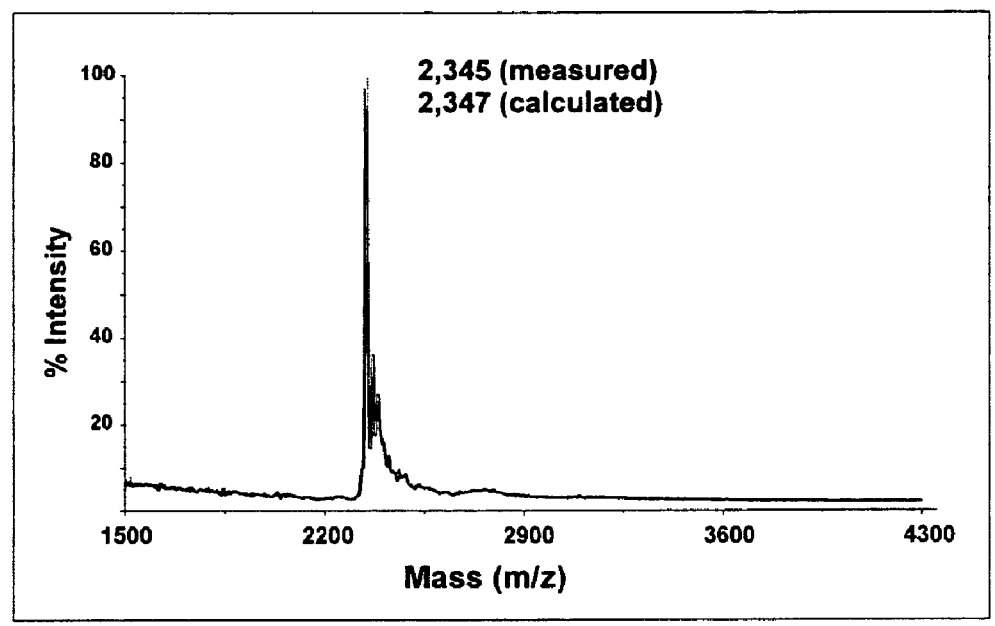
Figure 1:
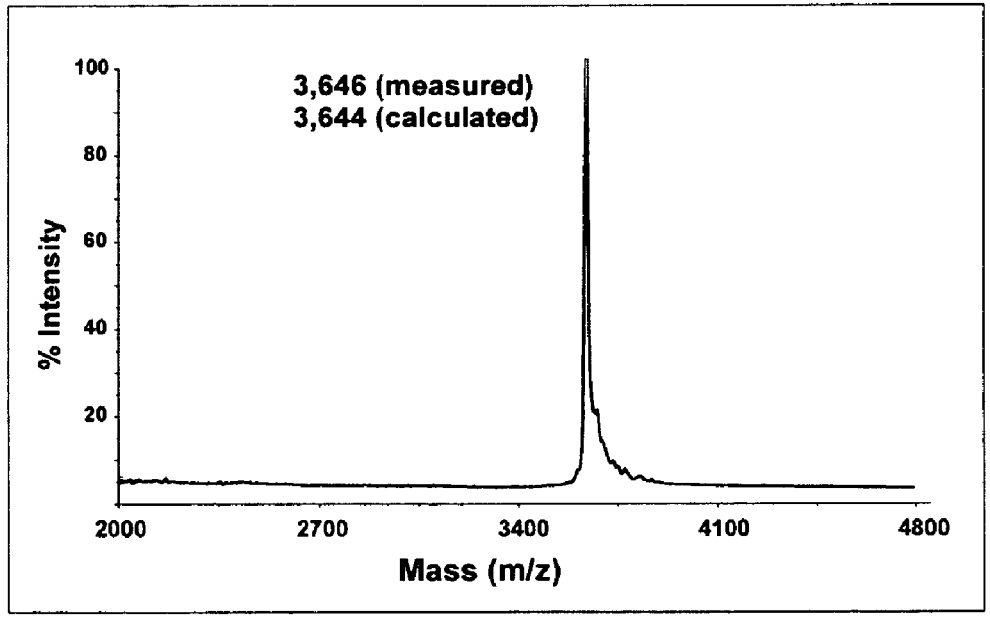

Substrate A = SEQ ID NO:30: Fl-<u>A</u>auggc<u>A</u>-QSY-7
Substrate B = SEQ ID NO:2: Fl-AuAA-Tamra

| Seq ID NO:2 | Seq ID NO:3 |
| --- | --- |
| Fl-AuAA-Tamra | Fl-AAuAA-Dabcyl |
| Composition: RNA + DNA | Composition: RNA + 2'OMe RNA |

+ DNase

+ RNase

Tapwater
Parts-per-thousand

With Buffer

Without Buffer

SEQ ID NO:30: Fl-AauggcA-QSY-7

SEQ ID NO:30: Fl-AauggcA-QSY-7

Stock RNase Diluted into a 100 μl Assay

RNase A
Stock: 1.0 μg/μl

RNase T1
Stock: 1000 units/μl

RNase 1
Stock: 100 units/μl

SEQ ID NO:30: Fl-AauggcA-QSY-7

SEQUENCE LISTING

```
<160> NUMBER OF SEQ ID NOS: 30

<210> SEQ ID NO 1
<211> LENGTH: 11
<212> TYPE: RNA
<213> ORGANISM: Artificial
<220> FEATURE:
<223> OTHER INFORMATION: Description of Artificial Sequence: Chimeric
                        RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
```

```
<221> NAME/KEY: modified_base
<222> LOCATION: 2, 3, 4, 5, 7, 8, 9, 10
<223> OTHER INFORMATION: a = 2'-O-methyl RNA base, adenosine
<220> FEATURE:
<221> NAME/KEY: modified_base
<222> LOCATION: 11
<223> OTHER INFORMATION: n = Rhodamine

<400> SEQUENCE: 1
naaaauaaaa n                                                                    11

<210> SEQ ID NO 2
<211> LENGTH: 6
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 4, 5
<223> OTHER INFORMATION: a = 2'-O-methyl RNA base, adenosine
<220> FEATURE:
<221> NAME/KEY: modified_base
<222> LOCATION: 6
<223> OTHER INFORMATION: n = Tamra

<400> SEQUENCE: 2 nauaan                                                                           6

<210> SEQ ID NO 3
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 3, 5, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 3 naauaan                                                                          7

<210> SEQ ID NO 4
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 3, 5, 6
<223> OTHER INFORMATION: a = 2'-O-methyl RNA base, adenosine
<220> FEATURE:
```

```
<221> NAME/KEY: modified_base
<222> LOCATION: 7
<223> OTHER INFORMATION: n = 4-(4'-dimethylaminophenylazo)benzoic acid

<400> SEQUENCE: 4 naagaan                                                                    7

<210> SEQ ID NO 5
<211> LENGTH: 7
<212> TYPE: RNA
<213> ORGANISM: Artificial
<220> FEATURE:
<223> OTHER INFORMATION: Description of Artificial Sequence: Chimeric
                        RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 3, 5, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 5 naacaan                                                                    7

<210> SEQ ID NO 6
<211> LENGTH: 7
<212> TYPE: RNA
<213> ORGANISM: Artificial
<220> FEATURE:
<223> OTHER INFORMATION: Description of Artificial Sequence: Chimeric
                        RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 3, 5, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 6 naaaaan                                                                    7

<210> SEQ ID NO 7
<211> LENGTH: 7
<212> TYPE: RNA
<213> ORGANISM: Artificial
<220> FEATURE:
<223> OTHER INFORMATION: Description of Artificial Sequence: Chimeric
                        RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 5, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid
```

-continued

```
<400> SEQUENCE: 7 naguaan                                                                    7

<210> SEQ ID NO 8
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 5, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 8 naacaan                                                                    7

<210> SEQ ID NO 9
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 5, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 9 nagaaan                                                                    7

<210> SEQ ID NO 10
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 6, 7
<223> OTHER INFORMATION: a = 2'-O-methyl RNA base, adenosine
<220> FEATURE:
<221> NAME/KEY: modified_base
<222> LOCATION: 8
<223> OTHER INFORMATION: n = 4-(4'-dimethylaminophenylazo)benzoic acid

<400> SEQUENCE: 10 nagucaan                                                                   8
```

```
<210> SEQ ID NO 11
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 6, 7
<223> OTHER INFORMATION: a = 2'-O-methyl RNA base, adenosine
<220> FEATURE:
<221> NAME/KEY: modified_base
<222> LOCATION: 8
<223> OTHER INFORMATION: n = 4-(4'-dimethylaminophenylazo)benzoic acid

<400> SEQUENCE: 11 nagcuaan                                                               8

<210> SEQ ID NO 12
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 12 nacgaan                                                                7

<210> SEQ ID NO 13
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 13 nacgcan                                                                7

<210> SEQ ID NO 14
<211> LENGTH: 7
<212> TYPE: RNA
```

```
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 14 nacggan                                                              7

<210> SEQ ID NO 15
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 15 nacguan                                                              7

<210> SEQ ID NO 16
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 16 nauagan                                                              7

<210> SEQ ID NO 17
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
```

```
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 17 nacuaan                                                                7

<210> SEQ ID NO 18
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 18 nucgaan                                                                7

<210> SEQ ID NO 19
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 7
<223> OTHER INFORMATION: a = 2'-O-methyl RNA base, adenosine
<220> FEATURE:
<221> NAME/KEY: modified_base
<222> LOCATION: 8
<223> OTHER INFORMATION: n = 4-(4'-dimethylaminophenylazo)benzoic acid

<400> SEQUENCE: 19 naucgaan                                                               8

<210> SEQ ID NO 20
<211> LENGTH: 7
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
```

```
<220> FEATURE:
<221> NAME/KEY: modified_base
<222> LOCATION: 6
<223> OTHER INFORMATION: a = 2'-O-methyl RNA base, adenosine
<220> FEATURE:
<221> NAME/KEY: modified_base
<222> LOCATION: 7
<223> OTHER INFORMATION: n = 4-(4'-dimethylaminophenylazo)benzoic acid

<400> SEQUENCE: 20 ncugaan                                                             7

<210> SEQ ID NO 21
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 7
<223> OTHER INFORMATION: a = 2'-O-methyl RNA base, adenosine
<220> FEATURE:
<221> NAME/KEY: modified_base
<222> LOCATION: 8
<223> OTHER INFORMATION: n = 4-(4'-dimethylaminophenylazo)benzoic acid

<400> SEQUENCE: 21 nacugaan                                                            8

<210> SEQ ID NO 22
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 7
<223> OTHER INFORMATION: a = 2'-O-methyl RNA base, adenosine
<220> FEATURE:
<221> NAME/KEY: modified_base
<222> LOCATION: 8
<223> OTHER INFORMATION: n = 4-(4'-dimethylaminophenylazo)benzoic acid

<400> SEQUENCE: 22 nagcuaan                                                            8

<210> SEQ ID NO 23
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 7
<223> OTHER INFORMATION: a = 2'-O-methyl RNA base, adenosine
```

```
<220> FEATURE:
<221> NAME/KEY: modified_base
<222> LOCATION: 8
<223> OTHER INFORMATION: n = 4-(4'-dimethylaminophenylazo)benzoic acid

<400> SEQUENCE: 23 nagucaan                                                                          8

<210> SEQ ID NO 24
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 7
<223> OTHER INFORMATION: a = 2'-O-methyl RNA base, adenosine
<220> FEATURE:
<221> NAME/KEY: modified_base
<222> LOCATION: 8
<223> OTHER INFORMATION: n = 4-(4'-dimethylaminophenylazo)benzoic acid

<400> SEQUENCE: 24 naagucan                                                                          8

<210> SEQ ID NO 25
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 7
<223> OTHER INFORMATION: a = 2'-O-methyl RNA base, adenosine
<220> FEATURE:
<221> NAME/KEY: modified_base
<222> LOCATION: 8
<223> OTHER INFORMATION: n = diarylrhodamine (QSY-7)

<400> SEQUENCE: 25 nagcuaan                                                                          8

<210> SEQ ID NO 26
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 7
<223> OTHER INFORMATION: a = 2'-O-methyl RNA base, adenosine
<220> FEATURE:
<221> NAME/KEY: modified_base
<222> LOCATION: 8
<223> OTHER INFORMATION: n = diarylrhodamine (QSY-7)
```

-continued

```
<400> SEQUENCE: 26 nagucaan                                                                    8

<210> SEQ ID NO 27
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 7
<223> OTHER INFORMATION: a = 2'-O-methyl RNA base, adenosine
<220> FEATURE:
<221> NAME/KEY: modified_base
<222> LOCATION: 8
<223> OTHER INFORMATION: n = diarylrhodamine (QSY-7)

<400> SEQUENCE: 27 naagucan                                                                    8

<210> SEQ ID NO 28
<211> LENGTH: 9
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 8
<223> OTHER INFORMATION: a = 2'-O-methyl RNA base, adenosine
<220> FEATURE:
<221> NAME/KEY: modified_base
<222> LOCATION: 9
<223> OTHER INFORMATION: n = diarylrhodamine (QSY-7)

<400> SEQUENCE: 28 naaggucan                                                                   9

<210> SEQ ID NO 29
<211> LENGTH: 8
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 7
<223> OTHER INFORMATION: a = 2'-O-methyl RNA base, adenosine
<220> FEATURE:
<221> NAME/KEY: modified_base
<222> LOCATION: 8
<223> OTHER INFORMATION: n = diarylrhodamine (QSY-7)

<400> SEQUENCE: 29 naaugcan                                                                    8
```

<210> SEQ ID NO 30
<211> LENGTH: 9
<212> TYPE: RNA
<213> ORGANISM: Artificial
<220> FEATURE:
<223> OTHER INFORMATION: Description of Artificial Sequence: Chimeric
      RNA Oligonucleotide Substrate
<220> FEATURE:
<221> NAME/KEY: modified_base
<222> LOCATION: 1
<223> OTHER INFORMATION: n = 6-carboxyfluorescein
<220> FEATURE:
<221> NAME/KEY: modified_base
<222> LOCATION: 2, 8
<223> OTHER INFORMATION: a = 2'-O-methyl RNA base, adenosine
<220> FEATURE:
<221> NAME/KEY: modified_base
<222> LOCATION: 9
<223> OTHER INFORMATION: n = diarylrhodamine (QSY-7)

<400> SEQUENCE: 30 naauggcan                                                               9

US 7,276,337 B2

COMPOSITIONS AND METHODS FOR VISUAL RIBONUCLEASE DETECTION ASSAYS

This application claims the benefit under 35 U.S.C. § 119(e) of U.S. Provisional Application No. 60/236,640 filed Sep. 29, 2000, which is incorporated by reference herein in its entirety.

1. INTRODUCTION

The present invention relates to methods for detecting the presence of ribonuclease enzymes, more specifically to methods that provide for a visual detection assay. The present invention further provides novel nucleic acid compositions used as substrates for such assays and encompasses kits for performing the methods of the invention.

2. BACKGROUND OF THE INVENTION

Ribonuclease (RNase) enzymes degrade polymeric ribonucleic acids (RNA) into shorter fragments or component nucleotides. All organisms produce ribonucleases and these enzymes are found in most environments. The properties of a number of ribonucleases are described by D'Alessio and Riordan (1997. As a group, most ribonucleases are specific for single-stranded RNA and will not cleave RNA in duplex form. Further, ribonucleases generally cleave at the 3'-end of a ribonucleic acid phosphodiester linkage. Many different RNase enzymes exist, some of which have little or no substrate preference while others are sequence specific. For example, ribonuclease I, from *E. coli*, is a non-specific endoribonuclease that degrades RNA by cleavage at any base. Ribonuclease A, from mammalian pancreas, is a base-specific endoribonuclease that degrades RNA by cleavage following a pyrimidine (uridine or cytosine) base. Ribonuclease T1, from *Aspergillus oryzae*, is a base-specific endoribonuclease that degrades RNA by cleavage following a guanosine residue. These three RNase enzymes are noteworthy in that they are routinely employed in standard molecular biology protocols to remove unwanted RNA from samples or as a component in certain assay procedures.

Single-strand specific RNases are the primary nuclease activity encountered in research laboratories as an unwanted contaminant. Double-strand specific RNases have been described, however these are rare and not routinely found in most laboratory settings. RNase H cleaves RNA only when complexed as a heteroduplex with DNA and is not of concern as a laboratory contaminant.

Ribonucleases are present in all laboratories as ubiquitous environmental contaminants. RNases are also found in most molecular biology laboratories as purified enzyme stocks. In laboratories that study RNA, careful attention to experimental protocol is needed to avoid contamination of reagents with RNases; for example, gloves must be worn at all times to prevent contact with the RNases that are universally present on human skin. Regardless of source, the presence of a contaminant RNase will degrade any RNA that comes in contact with that reagent, resulting in the loss of valuable samples or interfering with time-consuming experiments. Once present, removing RNase activity from a laboratory reagent is difficult. Most RNase enzymes are remarkably stable and survive harsh treatments that are routinely used to eliminate other unwanted biologic activities, such as autoclaving. Methods that remove RNase activity range from baking glassware at very high temperature to treating reagent stocks with the highly toxic chemical diethylpyrocarbonate (Sambrook et al., 1989). In spite of such attention, RNase contamination remains a chronic problem and monitoring for the presence of RNase activity is a routine quality control (QC) step in most research and industrial laboratories. As such, methods are needed that would detect the presence of RNase activities commonly encountered in the laboratory setting and that are suitable for routine, frequent use.

Many methods have been devised attempting to measure RNase activity. RNase assays can be grossly divided into methods that detect degradation of heterogeneous RNA obtained from biological sources and methods that detect specific cleavage of a well-defined synthetic substrate, such as an oligonucleotide. In general, use of a synthetic substrate affords both increased sensitivity and improved specificity. Many different detection modalities have been incorporated into these assays, including direct staining, spectrophotometric and colorimetric readouts, chromogenic cascade, radioactive tracer, fluorescence polarization, and fluorescence quenching methods.

Choice of detection method will affect assay sensitivity and ease of use. For use in determining the presence or absence of RNase contamination in laboratory reagents, the method should be sufficiently sensitive to detect the presence of RNase enzymes at the lowest level that will degrade experimental samples in actual use. An insensitive assay would "pass" reagents that are contaminated, which is undesirable. Conversely, an assay could be too sensitive and might "fail" reagents that, from a practical standpoint, are not contaminated and would therefore also be undesirable.

A detection limit within the range of 1-100 picogram/ml (pg/ml) of RNase A is ideal for a reagent QC assay. Commercial assays currently available are sensitive in the 10-100 pg/ml range (Ambion Catalog, 1999). Since such an assay would be used repeatedly, it is also desirable that the method be rapid and easy to perform. Preferably, such an assay could be done at the site of suspected contamination and offer a rapid visual readout.

The original unit definition of ribonuclease activity is based upon the method of Kunitz (1946) which employs a spectrophotometric assay to measure the decrease in absorbance at 300 nm that occurs with degradation of heterogeneous RNA. While the method has been improved (Oshima, 1976), it is insensitive and therefore of little use as a quality control (QC) assay.

Another method to detect RNase activity involves separation and assay of component enzyme activities within a sample using polyacrylamide gel electrophoresis (Wilson, 1969). RNase enzymes can be detected in the acrylamide matrix by direct staining or by incubation with a heterogeneous substrate RNA and an RNA staining dye, such as toluidine blue. While conceptually simple, this approach is time-consuming and relatively insensitive, having a lower limit of detection of about 1 unit of RNase I. In an improvement of this technique, Karpetsky (1980) describes a polynucleotide/polyacrylamide-gel electrophoresis method that improves sensitivity to below 100 pg of RNase A. However, even the improved method remains slow and cumbersome and is better suited to the analysis of ribonuclease activities in biologic specimens than to the QC of laboratory reagents.

Another approach to detect RNase activity is described by Egly and Kempf (1976). This procedure detects release of soluble $^{125}$Iodine-labeled RNA from an insoluble RNA-agarose matrix in the presence of ribonuclease. The method is capable of detecting the presence of RNase A at levels as low as 0.01 pg/ml and is actually too sensitive for use as a routine QC assay. Furthermore, this method employs a hazardous radioactive isotope as reporter that is not desirable for use in most laboratory or industrial settings.

Another approach to detect RNase activity is described by Wagner (1983). RNA forms a complex with Pyronine-Y that has an optical absorbance maximum at 572 nm. Degradation of high molecular weight RNA by ribonuclease activity results in loss of absorbance at 572 nm in a linear and quantitative fashion. The method, however, is only capable of detecting about 2 ng/ml RNase A in a test sample and has insufficient sensitivity for use as a QC assay.

Another approach to detect RNase activity was described by Greiner-Stoeffele (1996). The dye methylene blue intercalates into high molecular weight ribonucleic acid forming a dye-RNA complex. Upon degradation by ribonuclease action, methylene blue is released and absorbance at 688 nm decreases. This method, however, is also relatively insensitive and can detect ribonuclease activity only down to about 25 ng/ml, which is inadequate for use as a QC assay.

Another approach to detect RNase activity is described by Karn (1979). Ribonuclease A-mediated cleavage of a synthetic ribonucleotide dimer substrate was detected by a cascade of enzymatic reactions involving adenosine deaminase, nucleoside phosphorylase, and xanthine oxidase that ultimately forms a detectable blue tetrazolium salt. The method can detect the presence of 0.066 units of RNase A (about 100 ng), insufficient for use as a QC assay. Furthermore, the procedure is lengthy, complex and requires modification to detect the presence of ribonucleases other than RNase A.

Another approach to detect RNase activity is described by Witmer (1991). A synthetic ribonucleotide substrate, U-3'-BCIP, was synthesized that releases a reporter group in the presence of RNase A that could be detected spectrophotometrically by absorbance at 650 nm. While this chromogenic method is simple to use, it is insensitive and is better suited for applications such as the in vivo bacterial colony assays taught by Witmer than for use as a reagent QC assay.

Fluorescence-quenching detection is used in many applications in the biological sciences; representative examples include methods to detect proteolytic enzyme activity (Yaron, 1979), methods to detect DNA restriction endonuclease activity (Ghosh, 1994), methods to detect the 5'-nuclease activity of DNA polymerase (Gelfand, 1993), methods to detect nucleic acid sequence identity (Gelfand, 1993; Tyagi, 1999; Livak, 1999; Nazarenko, 1999; Nadeau, 1999), and methods to detect bimolecular protein interactions in an immunoassay (Maggio, 1980). A synthetic oligoribonucleotide having a Fam reporter group and a Tamra quencher group has been used as a FRET probe to detect hammerhead ribozyme activity (Hanne, 1998). Fluorescence Resonance Energy Transfer (FRET) and fluorescence quenching methods are reviewed by Morrison (1992).

Zelenko (1994) describes synthesis of a dinucleotide substrate uridylyl-3'5'-deoxyadenosine that is conjugated to a fluorophore (O-aminobenzoic acid) on one end and a fluorescence quencher (2,4-nitroaniline) on the opposite end of the molecule. Cleavage by RNase A separates the fluorophore and quencher, leading to a detectable increase in fluorescence. The substrate was designed specifically for use in kinetic studies of RNase A activity and will react only with the subset of ribonuclease enzymes that cleave at a uracil residue. Having a limited spectrum of sensitivity, this reagent is not suitable for use as a single substrate in an RNase QC assay.

James (1998) describe an alternative substrate for kinetic studies of RNase A in which a 9-mer chimeric oligonucleotide that contains a single ribonucleotide uracil base flanked by deoxyadenosine residues was modified with a 5' fluorescein reporter group and a 3' rhodamine quencher group. The utility of the substrate is limited in that it can detect only those ribonucleases that cleave at a uracil residue. Further, assay results must be detected using a fluorometer due to background fluorescence of the rhodamine quencher group.

Kelemen (1999) describes a similar substrate having somewhat greater sensitivity measuring RNase A kinetics with the following composition: SEQ ID. NO:2: 5' Fluorescein-AuAA-Tamra 3'. Like the James reagent, the Kelemen substrate is limited to detecting ribonucleases that cleave at a uracil residue and requires the use of a fluorometer.

James (1998) and Kelemen (1999), therefore, have described use of fluorescent-labeled oligonucleotide probes with FRET/quenching to study the catalytic properties of RNase A. Both compositions are chimeric DNA-RNA oligonucleotides that contain a single internal uridine base, use a fluorescein dye as reporter group, and use a quencher group that is a fluorophore that itself emits light in the visible spectrum, so methods that use these substrates require availability of a fluorometer for detection. These probes were optimized for kinetic studies of RNase A and cannot be used to detect the presence of RNase enzymes that do not cleave at a uridine residue. In addition, both compositions include DNA residues, which are subject to cleavage by DNase enzymes, so cleavage is not RNase specific. They are, therefore, not useful as a tool to assay for the presence of contaminating RNase activity.

Burke (1998) describes a method that utilizes fluorescence polarization detection techniques to measure cleavage of short, synthetic nucleic acid probes. A commercial kit for performing RNase detection of Burke is available (Pan Vera Catalog, 2000). Wilson (2000) describes a variant of this technique that examines real-time degradation of a long, synthetic RNA species (made by in vitro transcription) using fluorescence anisotropy. The fluorescence polarization-based techniques that must be employed, however, cannot be performed without a specialized fluorescence polarization fluorometer, which is not available in most laboratories.

Another commercial kit for the detection of RNase activity measures the release of soluble fluorescent dye from a precipitated (i.e., insoluble) fluorescent RNA substrate (Pan Vera Catalog, 2000). This method is less sensitive than the fluorescence polarization method and also requires availability of a fluorometer, thereby limiting the utility of the assay.

A commercial kit is available that uses a biotin-labeled RNA substrate immobilized on dipsticks to test for the presence of RNase activity (Ambion Catalog, 1999). Detection is achieved using a visual colorimetric method. In the absence of RNase, the substrate remains intact and the calorimetric assay develops a blue spot on the dipstick while in the presence of RNase the label is cleaved and no color develops. This assay is labor intensive, takes over 3 hours to perform, and is not well suited for high-throughput QC use.

Another commercial RNase detection kit employs gel electrophoresis to visualize degradation of a high molecular weight RNA in the presence of ribonuclease activity (Mo Bio, Web Catalog, 2000). The method is a multi-step, labor intensive protocol that is very expensive, making it unsuitable for routine QC use.

It is apparent from the above discussion that, while progress has been made in methodology to detect ribonuclease activity, existing assays have significant limitations.

None are suitable for use as a universal ribonuclease detection system (i.e., a QC assay). A ribonuclease detection method suitable for use in a QC assay should meet the following 7 criteria:
1) The assay will be highly sensitive.
2) The assay will be highly specific.
3) The assay will detect a broad spectrum of ribonuclease activities.
4) The assay reagent(s) will be inexpensive and suitable for commercial manufacture.
5) The assay method will be both simple and rapid.
6) The assay method will allow for visual detection and will not require the use of highly specialized equipment.
7) The assay will not employ any hazardous compounds.

Clearly new methods, or improvements in earlier methods, are needed. In particular, a need exists for an RNase assay that is rapid, sensitive, within the desired range and allows for visual detection.

3. SUMMARY OF THE INVENTION

The present invention describes novel nucleic acid compositions and methods for a fluorescence-quenching based assay of ribonuclease activity that overcomes the deficiencies of earlier teachings and is suitable for use as a research or industrial quality control assay. The method is highly sensitive, highly specific, capable of detecting a broad spectrum of ribonuclease enzymes, employs reagents that can be manufactured using commercial reagents, is rapid and easy to perform, does not use any hazardous reagents, and can be performed without any specialized equipment. Further, the method provides for a visual assay format. The visual assay is sensitive to 10 pg/ml RNase A, a level that is suitable for use as a QC assay. Surprisingly, sensitivity of the visual assay is comparable to that of existing commercial assays which require use of a fluorometer for detection. Compositions of the invention can also be used with fluorometric detection and are compatible with automated high-throughput robotic systems as are commonly employed in industrial settings.

The present invention further relates to novel nucleic acid compositions useful in the practice of such techniques and, still further, to kits for performing the method of the invention.

The present invention relates to methods for detecting ribonuclease activity in a sample, comprising: 1) incubating a of a synthetic Substrate or mixture of Substrates in the sample, for a time sufficient for cleavage of the Substrates(s) by a ribonuclease enzyme, wherein said Substrate(s) comprises a single-stranded nucleic acid molecule containing at least one ribonucleotide residue at an internal position that functions as a cleavage site, a fluorescence reporter group on one side of the cleavage sites, and a fluorescence-quenching group on the other side of the cleavage site, and 2) visual detection of a fluorescence signal, wherein detection of a fluorescence signal indicates that a ribonuclease cleavage event has occurred, and, therefore, the sample contains ribonuclease activity. The compositions of the invention are also compatible with other detection modalities (e.g., fluorometry).

The Substrate oligonucleotide of the invention comprises a fluorescent reporter group and a quencher group in such physical proximity that the fluorescence signal from the reporter group is suppressed by the quencher group. Cleavage of the Substrate with a ribonuclease enzyme leads to strand cleavage and physical separation of the reporter group from the quencher group. Separation of reporter and quencher eliminates quenching, resulting in an increase in fluorescence emission from the reporter group. When the quencher is a so-called "dark quencher", the resulting fluorescence signal can be detected by direct visual inspection. Cleavage of the Substrate compositions described in the present invention can also be detected by fluorometry.

In one embodiment, the synthetic Substrate is an oligonucleotide comprising ribonucleotide residues. The synthetic Substrate can also be a chimeric oligonucleotide comprising RNase-cleavable, e.g., RNA, residues, modified RNase-resistant RNA residues, or modified DNA residues that are resistant to cleavage by deoxyribonucleases. Substrate composition is such that cleavage is a ribonuclease-specific event and that cleavage by deoxyribonucleases does not occur.

In a preferred embodiment, the synthetic Substrate is a chimeric oligonucleotide comprising ribonucleotide residue(s) and modified ribonucleotide residue(s). In a more preferred embodiment, the synthetic Substrate is a chimeric oligonucleotide comprising ribonucleotide residues and 2'-O-methyl ribonucleotide residues. In a most preferred embodiment, the synthetic Substrate is a chimeric oligonucleotide comprising 2'-O-methyl ribonucleotide residues and one or more of each of the four ribonucleotide residues, adenosine, cytosine, guanosine, and uridine. Inclusion of the four distinct ribonucleotide bases in a single Substrate allows for detection of an increased spectrum of ribonuclease enzyme activities by a single Substrate oligonucleotide.

To enable visual detection methods, the quenching group is itself not capable of fluorescence emission, being a "dark quencher". Use of a "dark quencher" eliminates the background fluorescence of the intact Substrate that would otherwise occur as a result of energy transfer from the reporter fluorophore. In one preferred embodiment, the fluorescence quencher comprises dabcyl (4-(4'-dimethylaminophenylazo)benzoic acid). In a most preferred embodiment, the fluorescence quencher is comprised of QSY™-7 carboxylic acid, succinimidyl ester (N,N'-dimethyl-N,N'-diphenyl-4-((5-t-butoxycarbonylaminopentyl)aminocarbonyl) piperidinylsulfonerhodamine; a diarylrhodamine derivative from Molecular Probes, Eugene, Oreg.). Any suitable fluorophore may be used as reporter provided its spectral properties are favorable for use with the chosen quencher. A variety of fluorophores can be used as reporters, including but not limited to, fluorescein, tetrachlorofluorescein, hexachlorofluorescein, rhodamine, tetramethylrhodamine, Cy-dyes, Texas Red, Bodipy dyes, and Alexa dyes.

The method of the invention proceeds in two steps. First, the test sample is mixed with the Substrate reagent and incubated. Substrate can be mixed alone with the test sample or, more preferably, will be mixed with an appropriate buffer, e.g., one of a composition as described herein. Second, visual detection of fluorescence is performed. As fluorescence above background indicates fluorescence emission of the reaction product, i.e. the cleaved Substrate, detection of such fluorescence indicates that RNase activity is present in the test sample. The method provides that this step can be done with unassisted visual inspection. In particular, visual detection can be performed using a standard ultraviolet (UV) light source of the kind found in most molecular biology laboratories to provide fluorescence excitation. Substrates of the invention can also be utilized in assay formats in which detection of Substrate cleavage is done using a multi-well fluorescence plate reader or a tube fluorometer.

The present invention further features kits for detecting ribonuclease activity comprising a Substrate nucleic acid(s) and instructions for use. Such kits may optionally contain one or more of: a positive control ribonuclease, RNase-free water, and a buffer. It is also provided that said kits may include RNase-free laboratory plasticware, for example, thin-walled, UV transparent microtubes for use with the visual detection method and/or multiwell plates for use with plate-fluorometer detection methods in a high-throughput format.

Accordingly, the present invention provides a method for detecting ribonuclease activity in a test sample, comprising: (a) contacting the test sample with a substrate, thereby creating a test reaction mixture, wherein said substrate comprises a nucleic acid molecule comprising (i) a cleavage domain comprising a single-stranded region, said single-stranded region comprising at least one internucleotide linkage; (ii) a fluorescence reporter group on one side of the internucleotide linkage; and (iii) a non-fluorescent fluorescence-quenching group on the other side of the internucleotide linkage; (b) incubating said test reaction mixture for a time sufficient for cleavage of the substrate by a ribonuclease in the sample; and (c) determining whether a visually detectable fluorescence signal is emitted from the test reaction mixture, wherein emission of a fluorescence signal from the reaction mixture indicates that the sample contains ribonuclease activity.

While the methods of the invention can be practiced without the use of a control sample, in certain embodiments of the invention it is desirable to assay in parallel with the test sample a control sample comprising a known amount of RNase activity. Where the control sample is used as a negative control, the control sample preferably contains no detectable RNase activity. Thus, the present invention further provides a method for detecting ribonuclease activity in a test sample, comprising: (a) contacting the test sample with a substrate, thereby creating a test reaction mixture, wherein said substrate comprises a nucleic acid molecule comprising: (i) a cleavage domain comprising a single-stranded region, said single-stranded region comprising at least one internucleotide linkage; (ii) a fluorescence reporter group on one side of the internucleotide linkage; and (iii) a non-fluorescent fluorescence-quenching group on the other side of the internucleotide linkage; (b) incubating said test reaction mixture for a time sufficient for cleavage of the substrate by a ribonuclease activity in the test sample; (c) determining whether a visually detectable fluorescence signal is emitted from the test reaction mixture; (d) contacting a control sample with the substrate, said control sample comprising a predetermined amount of ribonuclease, thereby creating a control reaction mixture; (e) incubating said control reaction mixture for a time sufficient for cleavage of the substrate by a ribonuclease in the control sample; (f) determining whether a visually detectable fluorescence signal is emitted from the control reaction mixture; wherein detection of a greater fluorescence signal in the test reaction mixture than in the control reaction mixture indicates that the test sample contains greater ribonuclease activity than in the control sample, and wherein detection of a lesser fluorescence signal in the test reaction mixture than in the control reaction mixture indicates that the test sample contains less ribonuclease activity than in the control sample. In one embodiment, the predetermined amount of ribonuclease is no ribonuclease, such that detection of a greater fluorescence signal in the test reaction mixture than in the control reaction mixture indicates that the test sample contains ribonuclease activity.

The methods of the invention can further entail contacting the test sample with a buffer before or during step (a).

As stated above, the present invention further provides compositions and kits for practicing the present methods. Thus, in certain embodiments, the present invention provides a nucleic acid comprising: (a) a cleavage domain comprising a single-stranded region, said single-stranded region comprising at least one internucleotide linkage; (b) a fluorescence reporter group on one side of the internucleotide linkage; and (c) a non-fluorescent fluorescence-quenching group on the other side of the internucleotide linkage. In other embodiments, the present invention provides a kit comprising: (a) in one container, a substrate, said substrate comprising a nucleic acid molecule comprising a single stranded region, said single-stranded region comprising: (i) a cleavage domain comprising a single-stranded region, said single-stranded region comprising at least one internucleotide linkage 3' to an adenosine residue, at least one internucleotide linkage 3' to a cytosine residue, at least one internucleotide linkage 3' to a guanosine residue, and at least one internucleotide linkage 3' to a uridine residue, and wherein said cleavage domain does not comprise a deoxyribonuclease-cleavable internucleotide linkage; (ii) a fluorescence reporter group on one side of the internucleotide linkages; and (iii) a non-fluorescent fluorescence-quenching group on the other side of the internucleotide linkages.

In a preferred embodiment of the foregoing methods and compositions, the single stranded region of the cleavage domain comprises at least on internucleotide linkage 3' to an adenosine residue, at least one internucleotide linkage 3' to a cytosine residue, at least one internucleotide linkage 3' to a guanosine residue, and at least one internucleotide linkage 3' to a uridine residue. In another preferred embodiment, the cleavage domain does not comprise a deoxyribonuclease-cleavable internucleotide linkage. In yet another preferred embodiment, the single stranded region of the cleavage domain comprises at least on internucleotide linkage 3' to an adenosine residue, at least one internucleotide linkage 3' to a cytosine residue, at least one internucleotide linkage 3' to a guanosine residue, and at least one internucleotide linkage 3' to a uridine residue and the cleavage domain does not comprise a deoxyribonuclease-cleavable internucleotide linkage.

With respect to the fluorescence quenching group, any compound that is a dark quencher can be used in the methods and compositions of the invention. Numerous compounds are capable of fluorescence quenching, many of which are not themselves fluorescent, i.e., are dark quenchers.) In one embodiment, the fluorescence-quenching group is a nitrogen-substituted xanthene compound, a substituted 4-(phenyldiazenyl)phenylamine compound, or a substituted 4-(phenyldiazenyl)naphthylamine compound. In certain specific modes of the embodiment, the fluorescence-quenching group is 4-(4'-dimethylaminophenylazo)benzoic acid), N,N'-dimethyl-N,N'-diphenyl-4-((5-t-butoxycarbonylaminopentyl) aminocarbonyl) piperidinylsulfonerhodamine (sold as QSY-7™ by Molecular Probes, Eugene, Oreg.), 4',5'-dinitrofluorescein, pipecolic acid amide (sold as QSY-33™ by Molecular Probes, Eugene, Oreg.) 4-[4-nitrophenyldiazinyl]phenylamine, or 4-[4-nitrophenyldiazinyl]naphthylamine (sold by Epoch Biosciences, Bothell, Wash.). In other specific modes of the embodiment, the fluorescence-quenching group is Black-Hole Quencher™ 1, 2, or 3 (Biosearch Technologies, Inc.).

In certain embodiments, the fluorescence reporter group is fluorescein, tetrachlorofluorescein, hexachlorofluorescein, rhodamine, tetramethylrhodamine, a Cy dye, Texas Red, a Bodipy dye, or an Alexa dye.

With respect to the foregoing methods and compositions, the fluorescence reporter group or the fluorescence quenching group can be, but is not necessarily, attached to the 5'-terminal nucleotide of the substrate.

The nucleic acids of the invention, including those for use as substrates in the methods of the invention, are preferably single-stranded RNA molecule. In other embodiments, the nucleic acids of the invention are chimeric oligonucleotides comprising a nuclease resistant modified ribonucleotide residue. Exemplary RNase resistant modified ribonucleotide residues include 2'-O-methyl ribonucleotides, 2'-methoxyethoxy ribonucleotides, 2'-O-allyl ribonucleotides, 2'-O-pentyl ribonucleotides, and 2'-O-butyl ribonucleotides. In a preferred mode of the embodiment, the modified ribonucleotide residue is at the 5'-terminus or the 3'-terminus of the cleavage domain. In yet other embodiments, the nucleic acids of the invention are chimeric oligonucleotides comprising a deoxyribonuclease resistant modified deoxyribonucleotide residue. In specific modes of the embodiments, the deoxyribonuclease resistant modified deoxyribonucleotide residue is a phosphotriester deoxyribonucleotide, a methylphosphonate deoxyribonucleotide, a phosphoramidate deoxyribonucleotide, a phosphorothioate deoxyribonucleotide, a phosphorodithioate deoxyribonucleotide, or a boranophosphate deoxyribonucleotide. In yet other embodiments of the invention, the nucleic acids of the invention comprise an ribonuclease-cleavable modified ribonucleotide residue.

The nucleic acids of the invention, including those for use as substrates in the methods of the invention, are at least 3 nucleotides in length, but are more preferably 5-30 nucleotides in length. In certain specific embodiments, the nucleic acids of the invention are 5-20, 5-15, 5-10, 7-20, 7-15 or 7-10 nucleotides in length.

In certain embodiments, the fluorescence-quenching group of the nucleic acids of the invention is 5' to the cleavage domain and the fluorescence reporter group is 3' to the cleavage domain. In a specific embodiment, the fluorescence-quenching group is at the 5' terminus of the substrate. In another specific embodiment, the fluorescence reporter group is at the 3' terminus of the substrate.

In certain embodiments, the fluorescence reporter group of the nucleic acids of the invention is 5' to the cleavage domain and the fluorescence-quenching group is 3' to the cleavage domain. In a specific embodiment, the fluorescence reporter group is at the 5' terminus of the substrate. In another specific embodiment, the fluorescence-quenching group is at the 3' terminus of the substrate.

In a preferred embodiments of the invention, a nucleic acid of the invention comprising the formula: 5'-$N_1$-n-$N_2$-3', wherein: (a) "$N_1$" represents zero to five 2'-modified ribonucleotide residues; (b) "$N_2$" represents one to five 2'-modified ribonucleotide residues; and (c) "n" represents one to ten, more preferably four to ten unmodified ribonucleotide residues. In a certain specific embodiment, "$N_1$" represents one to five 2'-modified ribonucleotide residues. In preferred modes of the embodiment, the fluorescence-quenching group or the fluorescent reporter group is attached to the 5'-terminal 2'-modified ribonucleotide residue of $N_1$.

In the nucleic acids of the invention, including nucleic acids with the formula: 5'-$N_1$-n-$N_2$-3', the fluorescence-quenching group can be 5' to the cleavage domain and the fluorescence reporter group is 3' to the cleavage domain; alternatively, the fluorescence reporter group is 5' to the cleavage domain and the fluorescence-quenching group is 3' to the cleavage domain.

In embodiments where a nucleic acid of the invention comprises the formula 5'-$N_1$-n-$N_2$-3', the cleavage domain comprises the sequence "auggc" in a specific mode of such embodiments. In another specific mode of these embodiments, $N_1$ and $N_2$ each represent one 2'-modified ribonucleotide residue. The 2'-modified ribonucleotide residue is preferably an adenosine.

With respect to the kits of the invention, in addition to comprising a nucleic acid of the invention, the kits can further comprise one or more of the following: a ribonuclease; ribonuclease-free water; a buffer; and ribonuclease-free laboratory plasticware.

4. BRIEF DESCRIPTION OF THE DRAWINGS

FIG. 1: Mass spectroscopy traces of oligonucleotides. Following synthesis and purification, identity of SEQ ID NO:2 (panel A) and SEQ ID NO:30 (panel B) oligonucleotides were confirmed by mass spectroscopy analysis using a Voyager-DE MALDI-TOF mass spectroscopy workstation.

Figure 2:
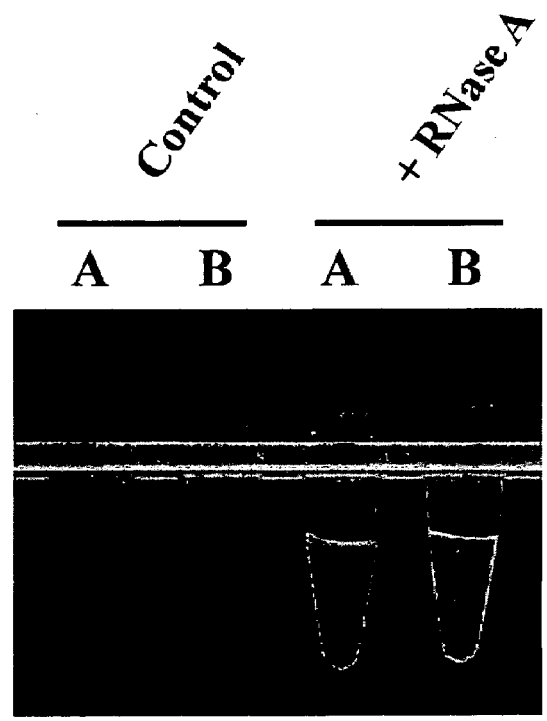

FIG. 2: Visual detection Assay for ribonuclease activity. Substrate oligonucleotide SEQ ID NO:30 which incorporates the dark quencher group QSY™-7 (A) and oligonucleotide SEQ ID NO:2 which incorporates Tamra, a quencher group that is itself fluorescent (B), were subjected to digestion with RNase A. Reactions were examined for fluorescence emission by visual inspection using an ultraviolet (UV) light source for excitation. Results were imaged by digital photography. Control reactions (without nuclease) are on the left and test reactions (with nuclease) are on the right.

Figure 3:
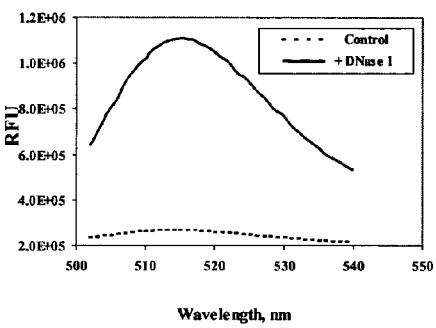
Figure 3:
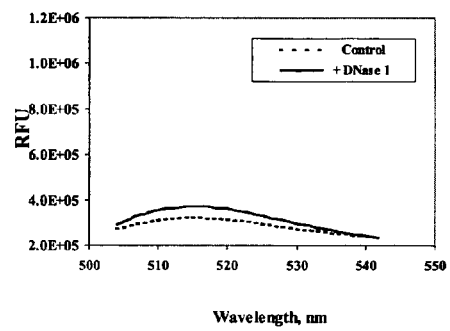
Figure 3:
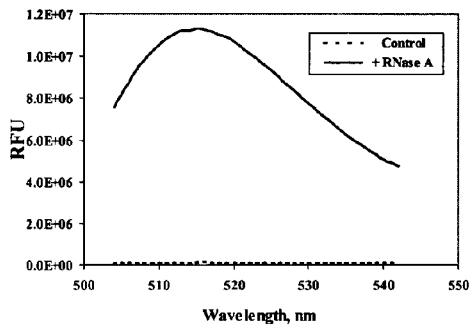
Figure 3:
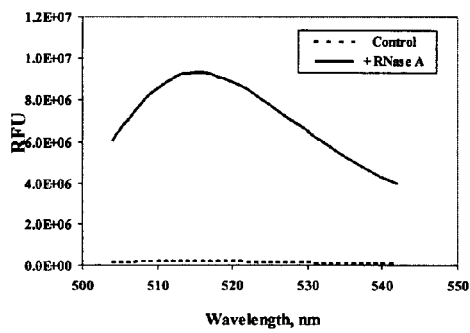

FIG. 3: Nuclease specificity of different oligonucleotides. Substrate oligonucleotide SEQ ID NO:2 having chimeric RNA-DNA composition (left panels) and Substrate oligonucleotide SEQ ID NO:3 having chimeric RNA-2'OMe-RNA composition. (right panels) were subjected to digestion with DNase 1 (top panels) or RNase A (bottom panels). Reactions were examined for fluorescence emission with 490 nm excitation using a cuvette fluorometer. Resulting emission spectra are expressed as relative fluorescence units (RFU). Control reactions (without nuclease) are represented by broken lines and test reactions (with nuclease) are represented by solid lines.

Figure 4:
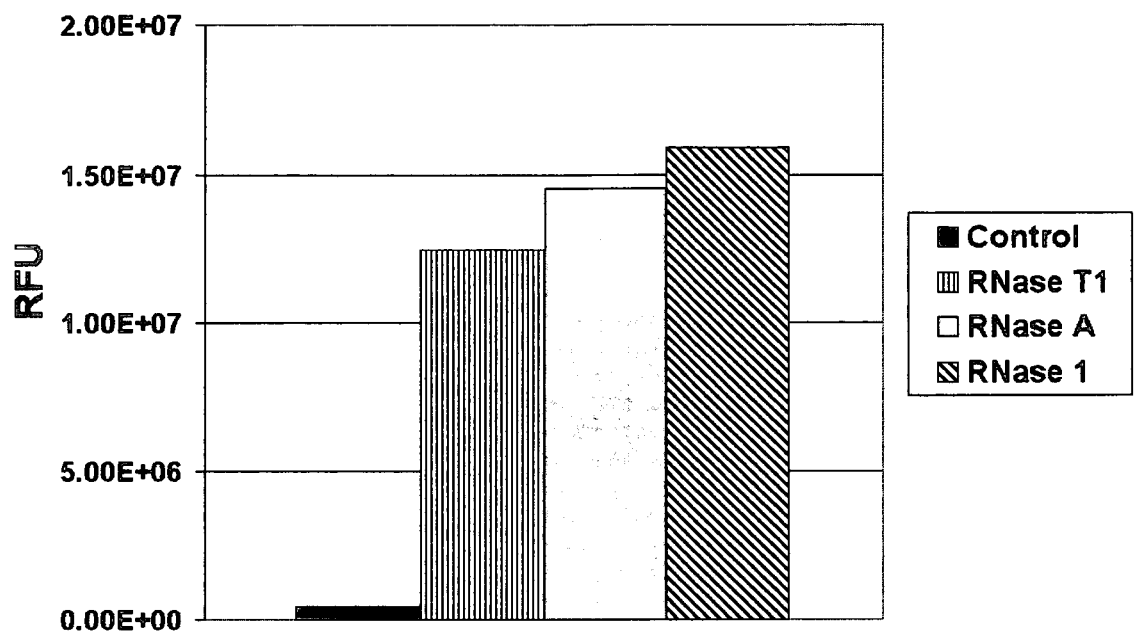

FIG. 4: Spectrum of ribonuclease sensitivity. Substrate oligonucleotide SEQ ID NO:30 having a 5 base ribonucleotide (auggc) cleavage domain was subjected to digestion with RNase A, RNase 1, or RNase T 1. Reactions were examined for fluorescence emission at 520 nm with 490 nm excitation using a cuvette fluorometer. Results are expressed as relative fluorescence units (RFU). Control reactions (without nuclease) are represented by solid black bars, RNase T1 reactions are represented by vertical-stripe bars, RNase A reactions are represented by solid gray bars, and RNase 1 reactions are represented by diagonal-stripe bars.

Figure 5:
Figure 5:

FIG. 5: Sensitivity of the assay improves with addition of buffer. Municipal water (tapwater) was tested for the presence of ribonuclease activity using the method of the invention. Substrate oligonucleotide SEQ ID NO:30 was incubated with dilutions of tapwater both with and without Assay Buffer. Reactions were examined for fluorescence emission by visual inspection using an ultraviolet (UV) light source for excitation. Results were imaged by digital photography.

Control reactions (without tapwater) are on the left and test reactions (with tapwater) proceed to the right.

Figure 6:
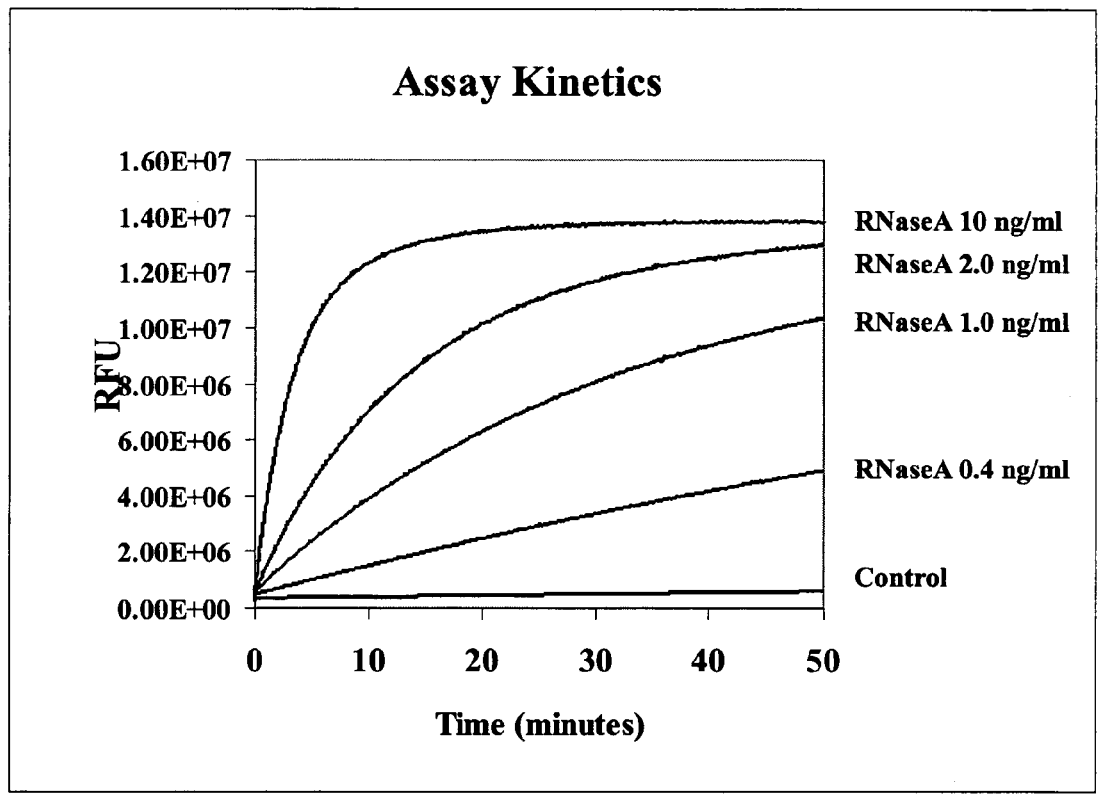

FIG. 6: Time course of the reaction. Substrate oligonucleotide SEQ ID NO:30, a preferred Substrate of the invention, was subjected to digestion with RNase A at concentrations of 10 ng/ml, 2 ng/ml, 1 ng/ml, and 0.4 ng/ml. Assays were examined for fluorescence emission at 520 nm with 490 nm excitation using a cuvette fluorometer while incubating at 37° C. Results are expressed as relative fluorescence units (RFU).

Figure 7:
Figure 7:

FIG. 7: Sensitivity of the visual detection method. Substrate oligonucleotide SEQ ID NO:30, the preferred Substrate of the invention, was subjected to digestion with RNase A, RNase 1, or RNase T1. Stock RNase enzymes were serial diluted. The final input mass for each reaction is indicated. Reactions were examined for fluorescence emission by visual inspection using an ultraviolet (UV) light source for excitation. Results were imaged by digital photography. Control reactions (without nuclease) are on the left and test reactions (with nuclease) proceed to the right.

5. DETAILED DESCRIPTION OF THE INVENTION

The present invention relates to methods for detecting the presence of ribonuclease enzyme activity. The present invention further relates to nucleic acid compositions that are Substrates for ribonuclease enzymes such that action of a ribonuclease enzyme on said Substrates results in a visibly detectable change in the Substrates using the method of the invention. Substrates specific for certain RNase enzyme activities can be used alone or in combination. The preferred embodiment of the invention provides for a composition comprising a fluorescent-labeled oligoribonucleotide Substrate that can serve as a universal reagent to detect many different ribonuclease enzymes.

The nucleic acid compositions of the invention contain pendant groups that allow for fluorescence-quenching detection methods using (FRET). A fluorescence reporter group and a fluorescence quencher group are physically connected by a chemical linkage that is cleaved during the course of the assay. Substrate cleavage leads to the physical separation of reporter and quencher, which results in loss of quenching effect and a concomitant rise in fluorescence signal by the reporter group.

The present invention relates to compositions and methods to detect ribonuclease activity suitable for use as a QC assay. It is desirable that a QC assay be simple, rapid, and easy to perform. Further, availability of a visual detection format limits the need for specialized equipment and permits use of the method by most users directly at the laboratory bench or in the field. The current invention provides for an RNase assay with direct visual readout that meets all of these needs and has the following properties:

1) Sensitivity: RNase activity is detected by cleavage of a synthetic Substrate oligonucleotide, said cleavage being sensitive to very low levels of ribonuclease.
2) Specificity: Substrate oligonucleotide is not cleaved by DNase; cleavage is limited to nucleases that cleave RNA and is therefore specific.
3) Spectrum: cleavage occurs after exposure to most ribonucleases.
4) Manufacture: the reagents employed can be manufactured using commercially available starting materials.
5) Complexity: the method is simple, rapid, and easy to perform.
6) Equipment: the assay can be done using visual detection and does not require use of any specialized equipment.
7) Safety: the method uses no hazardous chemicals or radioisotopes.

Compositions of the invention. Compositions of the invention comprise synthetic oligonucleotide Substrates that are substrates for ribonuclease enzymes. Substrate oligonucleotides of the invention comprise: 1) one or more RNase-cleavable bases, e.g., RNA bases, some or all of which function as scissile linkages, 2) a fluorescence-reporter group and a fluorescence-quencher group (in a combination and proximity that permits visual FRET-based fluorescence quenching detection methods), and 3) may optionally contain RNase-resistant modified RNA bases, or nuclease-resistant DNA bases. Synthetic oligonucleotide chimeras that contain RNA-DNA linkages have been described by Kempe (1982). Synthetic oligonucleotide RNA-DNA chimeras wherein the internal RNA bonds function as a scissile linkage are also described by Duck (1989).

Nucleic Acid Content. The Substrate is a synthetic (chemically synthesized) oligonucleotide, that generally ranges from about 3 nucleotides to about 30 nucleotides in length, with a preferred embodiment of about 3 to about 20 nucleotides, or about 3 to about 15 nucleotides, and contains both a fluorescence-reporter group and a fluorescence-quencher group. The fluorescence-reporter group and the fluorescence-quericher group are separated by at least one RNAse-cleavable residue, e.g., RNA base. Such residues serve as a cleavage domain for ribonucleases. In a preferred embodiment all 4 ribonucleotide residues are included within the cleavage domain.

At a minimum, the Substrate comprises at least one RNase-cleavable residue between the reporter and quencher groups. The nucleic acid content of the Substrate can comprise entirely RNA. Alternatively, the Substrate can include nuclease-resistant modified RNA residues, andor nuclease-resistant modified DNA residues. RNA residues may be continuous or interspersed. Modified residues that can be incorporated in the Substrate include, but are not limited to, 2'-O-methyl RNA, 2'-methoxyethoxy RNA, 2'-O-allyl RNA, 2'-O-pentyl RNA, 2'-O-butyl RNA, phosphotriester DNA, methylphosphonate DNA, phosphoramidate DNA, phosphorothioate DNA, phosphorodithioate DNA, and boranophosphate DNA.

The preferred composition is a chimeric RNA-2'-O-methyl RNA oligonucleotide having the general structure 5' r-NnN-q 3', where 'N' represents from about one to five 2'-modified ribonucleotide residues, 'n' represents one to ten unmodified ribonucleotide residues, 'r' represents a fluorescence reporter group, and 'q' represents a fluorescence quencher group. The 5'- and 3'-position of reporter and quencher are interchangeable. In the most preferred embodiment, all 4 RNA residues are present in a single Substrate, witin 'n' (i.e., base composition includes at least one each of the residues adenosine (a), cytosine (c), guanosine (g) and uridine (u)).

Nuclease Specificity. Oligonucleotides that contain DNA residues are subject to cleavage by DNase enzymes; it is desirable that a Substrate used in an RNase QC assay be ribonuclease specific. Compositions of the invention are therefore comprised entirely of nucleic acid residues that are not cleaved by DNase enzymes. RNase-cleavable residues, e.g., unmodified RNA residues, are included so that the Substrate oligonucleotide is subject to RNase cleavage.

Modified RNA residues can be included. If DNA residues are included, the DNA residues are modified in a way that confers resistance to cleavage by DNase enzymes. Compositions of the invention are, therefore, substrates for ribonuclease enzymes, but not deoxyribonuclease enzymes. For example, 2'-O-methyl RNA residues are not cleaved by deoxyribonuclease (Cummins, 1995) and so improve Substrate specificity compared with earlier compositions. Nuclease specificity of the invention is demonstrated in Example 2, FIG. 3, wherein an oligonucleotide containing both RNA and DNA residues is shown to be susceptible to DNase cleavage while Substrate compositions of the invention are resistant to DNase cleavage.

The RNase Cleavable Domain. An RNase-cleavable linkage, e.g., an RNA linkage, of one or more residues is positioned between the fluorescence reporter group and the fluorescence quencher group. Most ribonucleases catalyze cleavage of the phosphodiester bond on the 3'-side of an RNA residue. Cleavage of any linkage other than internucleoside phosphodiester bonds, such as the linkage between a terminal RNA residue and an attached pendant group, proceeds slowly if at all (Steyaert, 1991 a). An RNase-clevable linkage is therefore positioned such that cleavage of phosphodiester bonds between nucleic acids residues will separate reporter from quencher. It is preferred that all RNase-cleavable linkages, e.g., all RNA residues, lie internal to the reporter and quencher groups. For example, in a preferred Substrate, RNase-cleavable residues are positioned internally and function as a scissile domain, modified, nuclease-resistant, e.g., 2'-O-methyl RNA residue(s), terminate the RNase-cleavable, e.g., oligoribonucleotide, sequence at both the 5'- and 3'-ends, and a fluorescence reporter group and a fluorescence quencher group are attached to the terminal 2'-O-methyl RNA residues. The 2'-O-methyl RNA residues serve as attachment sites for the fluorescent groups and do not contribute to the scissile linkage. The Substrate may also be comprised entirely of RNase-cleavable, e.g., unmodified RNA residues.

It is preferred that at least one of each of the 4 RNA bases be included within the scissile linkage. Inclusion of all 4 bases expands the spectrum of RNase enzymes that will cleave the Substrate (Example 3, FIG. 4) and therefore expands the utility of the Substrate for RNase QC detection methods. Substrates are also envisioned which individually do not detect a broad range of ribonuclease enzymes but instead are optimized to detect the presence of a specific enzyme(s). A series of enzyme-specific Substrates can be used to detect a broad spectrum of ribonucleases; enzyme-specific Substrates can be used to characterize the nature of ribonuclease activity present in an unknown sample. For example, a set of 4 Substrates each comprising 'u', 'c', 'g', and 'a' would enable an RNase assay to identify and distinguish between RNase A, RNase T1, and RNase 1 activities. Such a specific assay is useful in identifying the source within a laboratory of a contaminating ribonuclease. The present invention, therefore, further includes such enzyme-specific Substrates, as well a methods for characterizing the nature of RNase activity in a sample.

Enzyme Specificity of the RNA Cleavable Domain. Most ribonuclease enzymes have an active site that binds a contiguous stretch of RNA several bases in length; enzyme-mediated cleavage occurs at a single residue within the bound sequence. Both RNase A and RNase T1 have substrate binding pockets that accommodate three bases (Wantanabe, 1985). The precise base sequence surrounding the cleavage site can influence the reaction (cleavage) rate. RNase A specifically cleaves after pyrimidine residues ('c' or 'u'). Cleavage rates are not equal at all 'c' or 'u' residues and substrates having composition "purine-pyrimidine-purine" are preferred, and even within this sequence 'a' is favored over 'g' (D'Alessio and Riordan, 1997). RNase T1 cleaves specifically after a guanosine ('g') base. Cleavage rates are reported to vary, favoring 'gc'>'ga'>'gu' (Steyaert, 1991b). With this in mind, a series of different Substrates with varying sequences were tested using RNase A, RNase T1, and RNase 1 for specificity and rate in Example 6. Base sequence was found to influence rate of cleavage, especially for RNase T1. New cleavage preferences for RNase T1 were defined that are distinct from the observations of Steyaert (1991b). The dinucleotide 'gg' was found to be more active than the other dinucleotide combinations tested. Sensitivity of the Substrate for cleavage by RNase T1 was 'gg'>'gc'>'ga'>'gu'. Of cleavable domains tested that contained a 'gg' dinucleotide, the triplet motif 'ggc' provided greater sensitivity than 'ggu'. Experimental testing defined a sequence optimized to cleave (i.e., detect) low levels of all three enzymes, which was more sensitive than other sequences examined. Relative cleavage rates (sensitivity) of Substrates having different sequence composition are described in Example 6, wherein a preferred Substrate of the invention is discussed.

The preferred composition for a single Substrate for use in the method of the invention is SEQ ID NO:30: 5'Fam-AauggcA-QSY™-7 3', where Fam is 6-carboxy-fluorescein, A is 2'-O-methyl adenosine, and 'a', 'c', 'u', 'g' are the ribonucleotide bases adenosine, cytosine, uridine, and guanosine. This composition has been experimentally tested and has very high cleavage rates and sensitivity to the presence of low levels of ribonucleases.

Most ribonucleases are specific for single-stranded RNA substrates. Therefore, it is preferred that a Substrate oligonucleotide not form a self-annealing hairpin or self-annealing dimer that includes the RNase-cleavable residues within the scissile domain. Compositions that favor hairpin or dimer formation according to standard Watson-Crick base-pairing rules can be readily identified and excluded by visual inspection or analysis using commonly available computer algorithms well known to those of skill in the art.

Reporter and Quencher Groups. The Substrate is further comprised of a fluorescence reporter group and a fluorescence quencher group that are covalently connected to each other by at least one RNase-cleavable linkage, e.g., as formed between two adjacent unmodified RNA residues, such that the residues comprise a scissile linkage wherein cleavage of this linkage results in physical dissociation of the fluorescence reporter group from the fluorescence quencher group. Compositions wherein a fluorescence reporter is in physical proximity to a fluorescence quencher result in suppression of fluorescence emission from the reporter; physical separation or dissociation of the fluorophore from the quencher removes this suppression. Following dissociation from the quencher, the fluorescence reporter emits light at a wavelength characteristic to that fluorophore (i.e., fluorescence emission) when stimulated by light at an appropriate wavelength (i.e., fluorescence excitation).

In the preferred embodiment, the fluorescence reporter group and the fluorescence quencher group are positioned at or near opposing ends of the molecule. It is not important which group is placed at or near the 5'-end versus the 3'-end. It is not required that the reporter and quencher groups be end modifications, however positioning these groups at termini simplifies manufacture of the Substrate. The fluorescence reporter group and the fluorescence quencher group may also be positioned internally so long as an RNA scissile linkage lies between reporter and quencher.

A fluorophore is a molecule that absorbs light (i.e. excites) at a characteristic wavelength and emits light (i.e. fluoresces) at a second lower-energy wavelength. Fluorescence reporter groups that can be incorporated into Substrate compositions include, but are not limited to, fluorescein, tetrachlorofluorescein, hexachlorofluorescein, tetramethylrhodamine, rhodamine, cyanine-derivative dyes, Texas Red, Bodipy, and Alexa dyes. Characteristic absorption and emission wavelengths for each of these are well known to those of skill in the art.

A fluorescence quencher is a molecule that absorbs or releases energy from an excited fluorophore (i.e., reporter), returning the fluorophore to a lower energy state without fluorescence emission at the wavelength characteristic of that fluorophore. For quenching to occur, reporter and quencher must be in physical proximity. When reporter and quencher are separated, energy absorbed by the reporter is no longer transferred to the quencher and is instead emitted as light at the wavelength characteristic of the reporter. Appearance of a fluorescent signal from the reporter group following removal of quenching is a detectable event and constitutes a "positive signal" in the assay of the present invention, and indicates the presence of RNase in a sample.

Fluorescence quencher groups include molecules that do not emit any fluorescence signal ("dark quenchers") as well as molecules that are themselves fluorophores ("fluorescent quenchers"). Substrate compositions that employ a "fluorescent quencher" will emit light both in the intact and cleaved states. In the intact state, energy captured by the reporter is transferred to the quencher via FRET and is emitted as light at a wavelength characteristic for the fluorescent quencher. In the cleaved state, energy captured by the reporter is emitted as light at a wavelength characteristic for the reporter. When compositions that employ fluorescent quenchers are used in a FRET assay, detection must be done using a fluorometer. Substrate compositions that employ a "dark quencher" will emit light only in the cleaved state, enabling signal detection to be performed visually (detection may also be done using a fluorometer). Visual detection is rapid, convenient, and does not require the availability of any specialized equipment. It is desirable for an RNase detection assay to have visual detection method as an available option. Example 1, FIG. 2 demonstrates that Substrate compositions employing a "dark quencher" enable a visual detection ribonuclease assay while Substrate compositions employing a "fluorescent quencher" are incompatible with a visual detection assay.

In the preferred embodiment of the invention, the Substrate is comprised of a fluorescence quencher group that does not itself emit a fluorescence signal, i.e. is a "dark quencher". "Dark quenchers" useful in compositions of the invention include, but are not limited to, dabcyl, QSY™-7, QSY-33 (4',5-dinitrofluorescein, pipecolic acid amide) and Black-Hole Quenchers™ 1,2, and 3 (Biosearch Technologies, Novato, Calif.). Assay results (i.e., signal from cleaved Substrate) can thus be detected visually. Optionally, the fluorescence signal can be detected using a fluorometer or any other device capable of detecting fluorescent light emission in a quantitative or qualitative fashion.

Substrate Synthesis. Synthesis of the nucleic acid Substrate of the invention can be performed using solid-phase phosphoramidite chemistry (Caruthers, 1992; Scaringe, 1990) with automated synthesizers, although other methods of nucleic acid synthesis (e.g., the H-phosphonate method) may be used. Chemical synthesis of nucleic acids allows for the production of various forms of the nucleic acids with modified linkages, chimeric compositions, and nonstandard bases or modifying groups attached in chosen places throughout the nucleic acid's entire length (Current Protocols in Molecular Biology). Methods for synthesis and purification of Substrate compositions of the invention are taught in Example 1.

Method. The method of the invention proceeds in the following steps: combine "test sample" with Substrate(s) to produce a mixture, said mixture being the Assay Mix, incubate, and detect fluorescence signal. "Test sample" refers to any material being assayed for ribonuclease activity and will preferably be a liquid. Solids can be indirectly tested for the presence of RNase contamination by washing or immersion in solvent, e.g., water, followed by assay of the solvent.

Assay Mix. The Substrate is mixed and incubated with the test sample. This mixture constitutes the Assay Mix. Ideally, the Assay Mix is a small volume, from about 1 ul to about 10 mls, or, more preferably from about 10 to 100 ul. The precise volume of the Assay Mix will vary with the nature of the test sample and the detection method. Optionally, a buffer can be added to the Assay Mix. Nucleases, including some ribonucleases, require the presence of divalent cations for maximum activity and providing an optimized buffered solution can increase the reaction rate and thereby increase assay sensitivity. Buffers of different composition can be used. One such non-limiting buffer is described in Example 1. The benefit of including buffer in the Assay Mix is demonstrated in Example 4, FIG. 5. Inclusion of control reactions is also preferred, but no essential. A Negative Control Mix, for example, comprises a solution of Substrate in water or buffer without any test sample or added nuclease. In this control, the Substrate should remain intact (i.e., without fluorescence emission). If the Negative Control Mix results in positive signal, then the quality of all reagents is suspect and fresh reagents should be employed. Possible causes of a signal in a Negative Control include degradation of the Substrate or contamination of any component reagent with ribonuclease activity. A Positive Control Mix, for example, comprises a solution of Substrate in water or buffer plus a known, active RNase enzyme. If the Positive Control Mix results in a negative signal, then the quality of all reagents is suspect and fresh reagents should be employed. Possible causes of a negative Positive Control Mix include defective Substrate or contamination of any component reagent with a ribonuclease inhibitor. Any RNase that cleaves the Substrate can be employed for use in the Positive Control Mix. In a preferred embodiment, RNase A is used, as this enzyme is both inexpensive and readily available. Alternatively, RNase 1 can be used. RNase 1 is heat labile and is more readily decontaminated from laboratory surfaces.

Incubation. The Assay Mix (e.g., the test sample plus Substrate) is incubated. Incubation time and condition can vary from a few minutes to 24 hours or longer depending upon the sensitivity required. Incubation times of one hour or less are desirable. Ribonucleases are catalytic. Increasing incubation time should therefore increase sensitivity of the Assay, provided that background cleavage of the Substrate (hydrolysis) remains low. Assay kinetics are examined in Example 5, FIG. 6. As is evident, assay background is stable over time and Assay sensitivity increases with time of incubation. Incubation temperature can generally vary from room temperature to 37° C. but may be adjusted to the temperature optimum of a specific ribonuclease suspected as being present as a contaminant.

Signal Detection. Fluorescence emission can be detected using a number of techniques (Morrison, 1992). The preferred method of detection is visual inspection. Visual detection is rapid, simple, and can be done without need of any specialized equipment. Alternatively, detection can be done using fluorometry or any other method that allows for qualitative or quantitative assessment of fluorescent emission.

Visual Detection Method. Following incubation, the Assay Mix is exposed to UV light to provide excitation of the fluorescence reporter group. An Assay Mix in which the Substrate remains intact will not emit fluorescent signal and will visually appear clear or dark. Absence of fluorescence signal constitutes a negative assay result. An Assay Mix in which the Substrate has been cleaved will emit fluorescent signal and will visually appear bright. Presence of fluorescence signal constitutes a positive assay result, and indicates the presence of RNase activity in he sample. The visual detection method is demonstrated in Example 1, FIG. 2. The visual detection method is primarily intended for use as a qualitative ribonuclease assay, with results being simply either "positive" or "negative". However, the assay is crudely quantitative in that a bright fluorescent signal indicates higher levels of RNase contamination than a weak fluorescent signal.

The Assay Mix will ideally constitute a relatively small volume, for example 10 to 100 μl, although greater or lesser volumes can be employed. Small volumes allow for maintaining high concentrations of Substrate yet conserves use of Substrate. The visual detection Assay as taught in Example 1 uses 50 pmoles of Substrate at a concentration of 0.5 uM in a 100 ul final volume Assay Mix. Lower concentration of Substrate (e.g., below 0.1 uM) will decrease assay sensitivity. Higher concentrations of Substrate (e.g., above 1 uM) will increase background and will unnecessarily consume Substrate.

Steps (mixing, incubating, detecting), can be performed in one tube. In a preferred embodiment, the tube is a small, thin-walled, UV transparent microfuge tube, although tubes of other configuration may be used. A "short wave" UV light source emitting at or around 254 nm is preferred for fluorescence excitation. A "long wave" UV light source emitting at or around 300 nm can also be employed. A high intensity, short wave UV light source will provide for best sensitivity. UV light sources of this kind are commonly found in most molecular biology laboratories. Visual detection can be performed at the laboratory bench or in the field, however sensitivity will be improved if done in the dark. Sensitivity of the visual detection method is demonstrated in Example 7, FIG. 7. Practical application of the visual detection assay in testing commercial laboratory reagents for RNase contamination is demonstrated in Example 8.

Fluorometric Detection Method. Following incubation fluorescence emission can be detected using a fluorometer. Fluorometric detection equipment includes, but is not limited to, single sample cuvette devices and multiwell plate readers. As before, mixing, incubation, and detection can be performed in the same vessel. Use of a multiwell plate format allows for small sample volumes, such as 200 μl or less, and high-throughput robotic processing of many samples at once. This format is preferred in industrial QC settings. The method also provides for the Assay to be performed in RNase free cuvettes. As before, mixing, incubation, and detection can be performed in the same vessel. Use of fluorometric detection allows for highly sensitive and quantitative detection. Sensitivity of the fluorometric detection is demonstrated in Example 7, Table 8.

Kits. The present invention further includes kits for detecting ribonuclease activity in a sample, comprising Substrate nucleic acid(s) and instructions for use. Such kits may optionally contain one or more of: a positive control ribonuclease, RNase-free water, a buffer, and other reagents. The kits may include RNase-free laboratory plasticware, such as thin-walled, UV transparent microtubes and/or multiwell plates for use with the visual detection method and multiwell plates for use with plate-fluorometer detection methods.

One kit of the invention includes a universal Substrate, said Substrate being sensitive to a broad spectrum of ribonuclease activity (e.g., Substrate oligonucleotide SEQ ID NO:30). The kit is intended to detect ribonuclease activity from a variety of sources. The assay is compatible with visual detection. Preferably, the Substrate will be provided in dry form in individual thin-walled, UV transparent microtubes, or in multiwell (e.g. 96 well) formats suitable for high throughput procedures. Lyophilized Substrate has improved long-term stability compared to liquid solution in water or buffer. If provided in liquid solution, stability is improved with storage at −20° C. or, more preferably, at −80° C. Storage in individual aliquots limits potential for contamination with environmental ribonucleases. Alternatively, the Substrate can be provided in bulk, either lyophilized or in liquid solution. Alternatively, substrate can be provided in bulk and can be dispersed at the discretion of the user.

An additional kit of the invention includes a set of enzyme-specific or enzyme-selective Substrates that together detect most RNase activities and individually can be used to distinguish between different ribonuclease enzymes. Such a kit can be used to assess the nature and source of RNase contamination or can measure activity of specific enzyme of interest.

The following examples are offered to further illustrate, but not limit, the methods and compositions of the invention, and serve to point out the unique features of the invention, which enable it to overcome limitations of earlier contributions to the field.

6. EXAMPLE 1

Synthesis and Use of Synthetic Oligonucleotide Substrate in a Visual Detection Ribonuclease Assay 6.1. Introduction Synthesis of novel Substrate compositions that employ "dark quenchers" and their use in the visual RNase detection method of the invention is described.

6.2. Materials and Methods

Oligonucleotide Synthesis: DNA β-cyanoethyl (CE) phosphoramidites were obtained from Perkin Elmer (Foster City, Calif.). RNA and 2'-O-methyl RNA phosphoramidites were obtained from Proligo, Inc. (Boulder, Colo.). 5'-Fluorescein phosphoramidite (6-FAM, 6-carboxyfluorescein) and Amino-modifier-C7 CPG was obtained from Glen Research (Sterling, Va.). 6-Carboxytetramethyl-rhodamine succinimidyl-ester (6-Tamra-NHS-ester) and QSY™ 7 carboxylic acid, succinimidyl ester were obtained from Molecular Probes (Eugene, Oreg.). Sephadex G25 Nap-10 chromatography columns were obtained from Amersham Pharmacia Biotech (Piscataway, N.J.).

Equipment used to synthesize the oligonucleotides of this Example include a Model 394 DNA/RNA Synthesizer (Applied Biosystems, Inc., Foster City, Calif.) and a Speed Vac Plus model SC210A rotary concentrator with Refrigerator Vapor Trap model RVT4104 (Savant Instrument Co., Holbrook, N.Y.). Purification was done using a Waters Model 600E High Performance Liquid Chromatography (HPLC) system (Millipore Corp., Milford, Mass.), equipped with a Hamilton PRP-1 column (Hamilton Co., Reno, Nev.) for reverse phase separations or a Source™ column (Amersham Pharmacia Biotech, Piscataway, N.J.) for ion-exchange separations. Compound identity was verified by mass spectroscopy using a Voyager-DE™ BioSpectrometry™ workstation (PerSeptive Biosystems, Inc., Foster City, Calif.).

RNase Assay: Reagents used to conduct the nuclease degradation experiments of this Example include oligonucleotides, enzymes, nuclease-free water, and Buffer. HPLC-grade water was obtained from Burdick and Jackson (Muskegon, Mich.). Assay Buffer was made as a 10× stock and diluted to 1× for use.

TABLE 1

Assay Buffer Composition

| Assay Buffer, 10× | Assay Buffer, 1× |
|---|---|
| 500 mM Tris, pH 7.0 | 50 mM Tris, pH 7.0 |
| 350 mM NaCl | 35 mM NaCl |
| 100 mM KCl | 10 mM KCl |
| 15 mM $MgCl_2$ | 1.5 mM $MgCl_2$ |
| 5 mM $CaCl_2$ | 0.5 mM $CaCl_2$ |
| 0.5% Triton X-100 | 0.05% Triton X-100 |

Equipment used to conduct the nuclease detection experiments of this Example include aerosol-barrier micropipette tips (RNase-free), micropipetters, thin-walled, UV transparent microtubes (RNase-free), a UV light source (Electronic Dual-Light™ Transilluminator, Ultra Lum, Carson, Calif.), and a digital camera (MVC-FD91, Sony Corp., Japan).

Nuclease enzymes: Nuclease enzymes employed in the Examples were obtained from Ambion, Inc., (Austin, Tex.), unless otherwise indicated and include:

TABLE 2

Nuclease Enzymes Employed in the Examples.

| Nuclease | Stock Concentration | Unit Definition |
|---|---|---|
| DNase 1 (RNase-free grade) | 2 units/ul | 1 unit of DNase 1 will result in an increase in A260 of 0.001 per minute when incubated with 40 ug/ml ssDNA at 25° C. |
| RNase A (RPA grade) | 1 ug/ul | 1 unit of RNase A will result in an increase in A286 of 0.0146 per minute when incubated with 1 mM cCMP in a volume of 1 ml. 1 Kunitz unit (Kunitz, 1946) is equal to about 7.5 cCMP units. |
| RNase 1 | 100 units/ul | 1 unit of RNase 1 will result in 50% degradation of a $^{32}$P-labeled RNA in vitro transcript mixed with 2 ug yeast RNA in a 30 minute incubation at 37° C. as measured by TCA precipitation. |
| RNase T1 | 1000 units/ul | 1 unit of RNase T1 will result in a change in A260 of 0.0004 per minute at room temperature of a 25 ug/ml solution of the dinucleotide GpA. |

6.3. Oligonucleotide Substrate Synthesis

The synthesis of oligonucleotides is described in this Example. The SEQ ID NO:2 oligonucleotide is a composition described by Kelemen (1999). Substrate SEQ ID NO:30 is the preferred Substrate of the invention as defined in Example 6.

SEQ ID NO:2: 5' Fluorescein-AuAA-Tamra 3'

SEQ ID NO:30: 5' Fluorescein-AauggcA-QSY-7 3'

Where A=deoxyadenosine (DNA), u=uridine, a=adenosine, g=guanine, c=cytosine (RNA), and A=2'-O-methyl adenosine (2'-O-methyl RNA). Oligonucleotide substrates were synthesized with a 6-carboxyfluorescein (6-FAM) at the 5'-end and an amino-modifier-C7 on the 3'-end using standard phosphoramidite chemistry on an Applied Biosystems Model 394 DNA/RNA synthesizer (Caruthers, 1992; Scaringe, 1990). Reactions were done on the 1 mmole scale.

Following synthesis, the controlled pore glass (CPG) solid support was transferred to a 2 ml microfuge tube. Oligonucleotides were cleaved from the CPG and deprotected by incubation for 2 hours at 65° C. in 1 ml of a 3:1 solution of $NH_4OH$/EtOH. The supernatant was removed and the CPG was washed with 1 ml of $EtOH/H_2O$ 3:1; supernatants were pooled and dried. The t-butyl-dimethyl-silyl protecting group was removed from RNA residues by treatment with 250 ul of fresh anhydrous triethylammonium-trihydrogen fluoride at room temperature in an ultrasonic bath for 2 hours. The oligonucleotide was precipitated by 1.5 ml of n-butanol; the sample was cooled at −70° C. for 1 hour then centrifuged at 10,000 g for 10 minutes. The supernatant was decanted and the pellet was washed again with n-butanol.

The oligonucleotides were then purified by reverse-phase HPLC using a linear gradient of acetonitrile in 0.1 M triethyl-ammonium acetate (TEAA) pH 7.2. The entire sample was loaded on a Hamilton PRP-1 column (1.0 cm×25 cm) and eluted with a linear 5% to 50% acetonitrile gradient over 40 minutes. Samples were monitored at 260 nm and 494 nm and peaks corresponding to the fluorescent-labeled oligonucleotide species were collected, pooled, and lyophilized.

The oligonucleotide samples were dissolved in 200 ul of sterile water and precipitated by adding 1 ml of 2% $LiClO_4$, followed by centrifuging at 10,000 g for 10 minutes. The supernatant was decanted; the pellet was washed with 10% aqueous acetone.

6-TAMRA succinimidyl-ester or QSYM 7 carboxylic acid, succinimidyl ester (0.1 ml of 10 mg/ml in dimethyl-sulfoxide) was mixed with the 3'-amino-modified oligonucleotide in 0.5 ml 50 mM sodium bicarbonate buffer, pH 8.5. The dye-labeling reaction was incubated for 12 hours at 37° C. Reactions were dried under vacuum. Labeled oligonucleotides were resuspended in 200 ul water and precipitated by adding 1 ml of 2% $LiClO_4$, followed by centrifuging at 10,000 g for 10 minutes in order to remove free dye.

The oligonucleotides were then purified by reverse-phase HPLC using conditions described above. Samples were monitored at 260 nm and 494 nm and peaks corresponding to the dual-labeled oligonucleotide species were collected, pooled, and lyophilized. The oligonucleotides were additionally purified by ion-exchange HPLC using a Source™ column (Amersham Pharmacia Biotech, Piscataway, N.J.) and eluted with a linear 0% to 50% 1 M LiCl gradient in 0.1 M Tris pH 8.0 over 40 minutes. Samples were monitored at 260 nm and 494 nm and peaks corresponding to the dual-labeled oligonucleotide species were collected, pooled, precipitated with 2% LiClO$_4$, and lyophilized.

Compound identify was verified after synthesis and purification by mass spectroscopy using a Voyager-DE BioSpectrometry workstation. Mass traces are shown in FIG. 1. Measured mass for Substrate SEQ ID NO:2 was 2345 (calculated mass 2347). Measured mass for Substrate SEQ ID NO:30 was 3646 (calculated mass 3644). Both masses are correct within the experimental error of the method and confirm identity of the products.

Other oligonucleotide Substrates used in subsequent Examples were synthesized, purified, and evaluated using the methods outlined above.

6.4. Visual Detection Method of the Nuclease Assay

Nuclease assays were conducted using the methods of the invention. SEQ ID NO:2 and SEQ ID NO:30 oligonucleotides were individually mixed in 1× Assay Buffer at a concentration of 500 nM (50 pmoles ODN in 100 ul volume) in thin-walled, UV transparent microtubes. RNase A (1 ul, diluted to 0;1 ug/ul) was added to the respective Assay Mixes. Negative Control reactions did not receive nuclease. Assays were set up directly in microtubes as follows:

TABLE 3

Composition of Assay Mixtures, Example 1

| Item | Amount | Final |
| --- | --- | --- |
| Substrate | 50 pmoles (dry) | 500 nM |
| 10× Assay Buffer | 10 ul | 1× |
| Water | 89 ul | |
| Nuclease: RNase A | 1 ul (0.1 ug) | 1.0 ug/ml |
| Final Volume | 100 ul | |

Assay Mixes were incubated at room temperature for 10 minutes. Assays were visually examined for fluorescence emission directly in the assay tubes without further manipulation. Tubes were suspended above an ultraviolet light source, visually inspected, and photographed using a digital camera. Results are shown in FIG. 2. The Substrate of the present invention (SEQ ID NO:30) appeared visually transparent (dark) in the absence of RNase (control reaction). In the presence of RNase, this Substrate emitted a fluorescent signal that was visibly bright. The "positive" and "control" reactions appeared markedly different and were easily distinguished. SEQ ID NO:2, in contrast, emitted light in the absence of RNase; in the presence of RNase, fluorescence emission changed somewhat in color and slightly increased in intensity. The "positive" and "control" reactions were not markedly different to visual inspection. As is evident from these results, compositions comprising quencher groups that are themselves fluorescent are not suitable for use in visual assay formats while compositions comprising dark quencher groups can be used in a visual assay format as per the method of the invention.

7. EXAMPLE 2

Reaction Specificity: DNase vs. RNase

7.1. Introduction

It is desirable that Substrate(s) used in a ribonuclease assay be ribonuclease specific substrates. Compositions of the present invention do not contain residues susceptible to DNase attack. This example demonstrates that oligonucleotides that contain unmodified DNA, are cleaved by DNase while compositions of the present invention are RNase specific.

7.2. Materials and Reagents

Reagents used to conduct the nuclease degradation experiments of this Example include oligonucleotides, DNase I, RNase A, nuclease-free water, and Buffer. Two oligonucleotides were employed, including:

```
SEQ ID NO:2:   5' Fluorescein-AuAA-Tamra 3'

SEQ ID NO:3:   5' Fluorescein-AAuAA-Dabcyl 3'
```

Where: A=deoxyadenosine (DNA), u=uridine (RNA), and A=2'-O-methyl adenosine (2'-O-methyl RNA). SEQ ID NO:2 is a composition described by Kelemen (1999). Substrate SEQ ID NO:3 is a novel Substrate composition of this Example. Oligonucleotides were synthesized and purified as outlined in Example 1, Section 6.3. Water was HPLC-grade from Burdick and Jackson (Muskegon, Mich.).

Equipment used to conduct the nuclease detection experiments of this Example include a water bath set to 37° C., aerosol-barrier micropipette tips (RNase-free), micropipetters, disposable cuvettes (RNase-free) and a cuvette fluorometer (Photon Technology International, Monmouth Jct., N.J.).

7.3. Nuclease Assay

Nuclease assays were conducted using the method of the invention. SEQ ID NO:2 and SEQ ID NO:3 oligonucleotides were individually mixed in 1× Assay Buffer at a concentration of 50 nM (150 pmoles oligonucleotide in 3 mls volume). Test nucleases were added to respective Assay Mixes, either 6 units of DNase 1 or 1 ug of RNase A. Negative Control reactions did not receive nuclease. Assays were set up directly in cuvettes as follows:

TABLE 4

Components of Assay Mixtures, Example 2.

| Item | Amount | Final |
| --- | --- | --- |
| Substrate | 3 ul (50 pmoles/ul) | 50 nM |
| 10× Assay Buffer | 300 ul | 1× |
| Water | 1.7 ml | |
| Nuclease: | 3 ul (6 units) | 2 units/ml |
| DNase I | 1 ul (1 ug) | 0.33 ug/ml |
| RNase A | | |
| Final Volume | | 3 mls |

Assay Mixes were incubated at 37° C. for 1 hour. Fluorescence emission spectra were measured using a PTI fluorometer with 490 nm excitation. Results are shown in FIG. 3. Substrate SEQ ID NO:2 (having chimeric RNA-DNA composition) reacted with both DNase I (undesired) and RNase A (desired). Substrate SEQ ID NO:3 (containing RNA-2'OMe-RNA and no DNA) did not react with DNase I but retained reactivity with RNase A, verifying that Substrate compositions of the invention are RNase specific.

8. EXAMPLE 3

Reaction Specificity: Detection of Various Ribonuclease Enzymes 8.1. Introduction It is desirable that Substrate(s) used in a ribonuclease QC assay be sensitive to a broad range of ribonuclease activities. The present example demonstrates that a single Substrate can be designed that detects multiple ribonuclease enzymes.

8.2. Materials and Reagents

Reagents used to conduct the nuclease degradation experiments of this Example include a Substrate oligonucleotide, enzymes, nuclease-free water, and Buffer. The Substrate oligonucleotides employed was:

SEQ ID NO:30: 5' Fluorescein-AauggcA-QSY-7 3'

Where: u=uridine, a=adenosine, g=guanosine, c=cytosine (RNA), and A=2'-O-methyl adenosine (2'-O-methyl RNA). Substrate SEQ ID NO:30 is the preferred Substrate of the invention as defined in Example 6.

Equipment used to conduct the nuclease detection experiments of this Example include a water bath set to 37° C., aerosol-barrier micropipette tips (RNase-free), micropipetters, disposable cuvettes (RNase-free) and a fluorometer (Photon Technology International, Monmouth Jct., N.J.).

8.3. Nuclease Assay

Nuclease assays were conducted using the method of the invention. The Substrate (SEQ ID NO:30) was mixed in 1× Assay Buffer at a concentration of 50 nM (150 pmoles oligonucleotide in 3 mls volume). Test nucleases were added to respective Assay Mixes, including 1 ul of RNase A (1 ug), 1 ul of RNase 1 (100 units), or 1 ul of RNase T1 (1000 units). Negative Control reactions did not receive nuclease. Assays were set up directly in cuvettes as follows:

TABLE 5

Components of Assay Mixtures, Example 3.

| Item | Amount | Final |
|---|---|---|
| Substrate | 3 ul (50 pmoles/ul) | 50 nM |
| 10× Assay Buffer | 300 ul | 1× |
| Water | 2.7 ml | |
| Nuclease: | | |
| RNase A | 1 ul (1 ug) | 0.33 ug/ml |
| RNase 1 | 1 ul (100 units) | 33 units/ml |
| RNase T1 | 1 ul (1000 units) | 333 units/ml |
| Final Volume | | 3 mls |

Assay Mixes were incubated at 37° C. for 1 hour. Assays were transferred to cuvettes and fluorescence emission at 520 nm was measured using a PTI fluorometer with 490 nm excitation. Results are shown in FIG. 4. Substrate SEQ ID NO:30, a preferred Substrate of the invention, reacted with (i.e., detected) all three RNase enzymes, verifying that Substrate compositions of the invention are sensitive to a variety of RNase enzymes.

9. EXAMPLE 4

Improved Assay Sensitivity with Addition of Buffer 9.1. Introduction

The Assay uses a synthetic oligonucleotide Substrate to test samples for the presence of ribonuclease enzymes. Enzymatic cleavage of the Substrate by a ribonuclease results in a detectable change in the Substrate. Assay conditions can influence enzyme activity and therefore influence Assay sensitivity. Most ribonuclease enzymes have a pH optimum between 6.0 and 7.5. Some require the presence of divalent cations for maximal activity. Fluorescein (the reporter group employed in a preferred Substrate of the invention) has optimal fluorescence activity at pH 7 or above. Not all test samples will have a composition that is optimal to assay for the presence of ribonuclease enzyme activity. Therefore, the method of the invention provides for an Assay Buffer that can optionally be added to the Assay Mix, which can improve Assay sensitivity with some test samples.

9.2. Materials and Reagents

Reagents used to conduct the ribonuclease detection experiments of this Example include a Substrate oligonucleotide, nuclease-free water, Buffer, and test sample. The Substrate oligonucleotide employed was:

SEQ ID NO:30: 5' Fluorescein-AauggcA-QSY-7 3'

Where: u=uridine, a=adenosine, g=guanosine, c=cytosine (RNA), and A=2'-O-methyl adenosine (2'-O-methyl RNA). Substrate SEQ ID NO:30 is a preferred Substrate of the invention as defined in Example 6. The Substrate was synthesized and purified as outlined in Example 1, Section 6.3. RNase-free water was obtained from Burdick and Jackson (Muskegon, Mich.). Assay Buffer was described in Example 1, section 6.2 above. The test sample was water obtained from a municipal water supply (i.e., tapwater, Coralville, Iowa).

Equipment used to conduct the Assay include aerosol-barrier micropipette tips (RNase-free), micropipetters, thin-walled, UV transparent microtubes (RNase-free), a UV light source (Electronic Dual-Light™ Transilluminator, Ultra Lum, Carson, Calif.), and a digital camera (MVC-FD91, Sony Corp., Japan).

9.3. Ribonuclease Assay on an Environmental Sample

Nuclease assays were conducted using the method of the invention. Dilutions of the test sample (tapwater) were made in nuclease-free water both with and without the addition of Assay Buffer. Samples were tested having 100%, 50%, 25%, 10%, 5%, and 1% tapwater. Assay Mixes contained test sample (diluted or undiluted tapwater) and Substrate (SEQ ID NO:30) at a concentration of 500 nM (50 pmoles ODN in 100 ul volume). Control Assay Mixes were in nuclease-free water without added tapwater. Duplicate Assays were performed with and without 1× Assay Buffer. Assay Mixes were incubated at room temperature for 10 minutes. Reactions were visually examined for fluorescence emission in the assay tubes without further manipulation. Tubes were suspended above an ultraviolet light source, visually inspected, and photographed using a digital camera. Results are shown in FIG. 5. The control reactions (without tapwater) appeared visually transparent (dark). The test samples (with tapwater) emitted fluorescent signal. With Assay Buffer, tapwater was detectable when diluted to as little as 10 parts-per-thousand (1%). Without Assay Buffer, the assay was less sensitive and fluorescent emission was less intense. Addition of Buffer thus led to improved assay sensitivity.

10. EXAMPLE 5

Time Course of the Assay 10.1. Introduction

Ribonucleases are catalytic and cleavage proceeds over time. High concentrations of nuclease will rapidly cleave the Substrate. Low concentrations of nuclease will cleave the Substrate gradually over time. Extended incubation should therefore increase sensitivity of the Assay as measured at the endpoint. Extended incubation will only increase Assay sensitivity, however, if background (i.e., hydrolysis of the Substrate) remains low. Assay kinetics were examined. Assay background was found to remain stable over time and Assay sensitivity increased with incubation.

10.2. Materials and Reagents

Reagents used to conduct the ribonuclease detection experiments of this Example include a Substrate oligonucleotide, nuclease-free water, Buffer, and ribonuclease. The Substrate oligonucleotide employed was:

SEQ ID NO:30: 5' Fluorescein-AauggcA-QSY-7 3', the preferred Substrate of the invention. Similar equipment was used as in previous Examples.

10.3. Measurements of the Assay during Real Time

Substrate SEQ ID NO:30 was mixed in 1× Assay Buffer at a concentration of 50 nM (150 pmoles oligonucleotide in 3 mls volume). RNase A was added at final concentrations of 10 ng/ml, 2 ng/ml, 1 ng/ml, and 0.4 ng/ml. The Control reaction did not receive any added ribonuclease. Assay mixes were incubated at 37° C. in a cuvette directly in a PTI fluorometer. Fluorescence emission at 520 nm with 490 nm excitation was measured over time. Results are shown in FIG. 6. At high nuclease concentrations, the reaction goes rapidly to completion. At lower nuclease concentrations, the reaction rate decreases but with longer incubation times an easily detectable signal is generated. Substrate concentration is fixed and input enzyme (i.e., the test sample) varies. Since the background is stable (monitored in the control reaction), use of extended incubation periods will increase the sensitivity of the assay.

The method of the invention provides a visual Assay, which is both rapid and simple. The Assay is also compatible with quantitative analysis if fluorometric detection is employed. Samples containing large amounts of RNase activity may require dilution to obtain quantitative results. Samples containing very low amounts of RNase activity can be assayed with extended incubation.

11. EXAMPLE 6

Substrate Optimization 11.1. Introduction

Some ribonuclease enzymes are sequence non-specific while others are sequence specific. Reaction specificity and rate can both be influenced by Substrate sequence. An ideal Substrate will be cleaved by a broad spectrum of ribonucleases. A variety of Substrates were designed, synthesized, and tested to determine the relative effect that sequence and other design elements have on Assay sensitivity. Sequence motifs that increase sensitivity to RNase T1 were defined. A preferred Substrate was identified.

11.2. Materials and Reagents

Reagents used to conduct the nuclease degradation experiments of this Example include 28 Substrate oligonucleotides. Equipment used was similar to previous Examples.

Twenty-eight Substrate oligonucleotides having "dark quencher" groups at the 3'-end were synthesized and tested, including:

SEQ ID NO:3:   5' Fluorescein-AAuAA-Dabcyl 3'
SEQ ID NO:4:   5' Fluorescein-AAgAA-Dabcyl 3'
SEQ ID NO:5:   5' Fluorescein-AAcAA-Dabcyl 3'
SEQ ID NO:6:   5' Fluorescein-AAaAA-Dabcyl 3'
SEQ ID NO:7:   5' Fluorescein-AguAA-Dabcyl 3'
SEQ ID NO:8:   5' Fluorescein-AacAA-Dabcyl 3'
SEQ ID NO:9:   5' Fluorescein-AgaAA-Dabcyl 3'
SEQ ID NO:10:  5' Fluorescein-AgucAA-Dabcyl 3'
SEQ ID NO:11:  5' Fluorescein-AgcuAA-Dabcyl 3'
SEQ ID NO:12:  5' Fluorescein-AcgaA-Dabcyl 3'
SEQ ID NO:13:  5' Fluorescein-AcgcA-Dabcyl 3'
SEQ ID NO:14:  5' Fluorescein-AcggA-Dabcyl 3'
SEQ ID NO:15:  5' Fluorescein-AcguA-Dabcyl 3'
SEQ ID NO:16:  5' Fluorescein-AuagA-Dabcyl 3'
SEQ ID NO:17:  5' Fluorescein-AcuaA-Dabcyl 3'
SEQ ID NO:18:  5' Fluorescein-ucgaA-Dabcyl 3'
SEQ ID NO:19:  5' Fluorescein-AucgaA-Dabcyl 3'
SEQ ID NO:20:  5' Fluorescein-cugaA-Dabcyl 3'
SEQ ID NO:21:  5' Fluorescein-AcugaA-Dabcyl 3'
SEQ ID NO:22:  5' Fluorescein-AgcuaA-Dabcyl 3'
SEQ ID NO:23:  5' Fluorescein-AgucaA-Dabcyl 3'
SEQ ID NO:24:  5' Fluorescein-AagucA-Dabcyl 3'
SEQ ID NO:25:  5' Fluorescein-AgcuaA-QSY-7 3'
SEQ ID NO:26:  5' Fluorescein-AgucaA-QSY-7 3'
SEQ ID NO:27:  5' Fluorescein-AagucA-QSY-7 3'
SEQ ID NO:28:  5' Fluorescein-AagucA-QSY-7 3'
SEQ ID NO:29:  5' Fluorescein-AaugcA-QSY-7 3'
SEQ ID NO:30:  5' Fluorescein-AauggcA-QSY-7 3'

Where: agcu = RNA bases, adenosine, guanosine, cytosine, and uridine
A = 2'-O-methyl RNA base, adenosine
Dabcyl = 4-(4'-dimethylaminophenylazo)benzoic acid
QSY™-7 = diarylrhodamine (Molecular Probes)
Fluorescein = 6-FAM, 6-carboxyfluorescein Oligonucleotides were synthesized and purified as outlined in Example 1, Section 6.3.

11.3. Substrate Optimization in Ribonuclease Assays

Nuclease assays were conducted using the method of the invention with both visual and fluorometric detection methods. Substrates were individually mixed in 1× Assay Buffer at a concentration of 50 nM (50 pmoles oligonucleotide in 1 ml volume) for fluorometric detection or at a concentration of 500 nM (50 pmoles of oligonucleotide in 100 ul volume) for visual detection. Test nucleases were added to respective Assay Mixes beginning at 1 ul stock reagent and proceeding with a 1:10 serial dilution until undetectable. Reaction mixes were incubated at 37° C. for 60 minutes. Fluorometric detection was performed as outlined in Example 2. Visual detection was performed as outlined in Example 1.

Different Substrates were examined for reactivity with RNase A, RNase 1, and RNase T1. A Substrate composition that contains all 4 ribonucleotide bases in an optimized sequence might be sensitive to most ribonuclease activities and could function as a stand-alone reagent for the Assay. Alternatively, a mix of Substrates could be used (for example, wherein one Substrate contains adenosine, one contains guanosine, one contains uridine, and one contains cytosine residues). Both possibilities were tested. A single Substrate that incorporates all 4 bases was found to be more sensitive to detecting the presence of ribonuclease activity than was a mixture of shorter Substrates. Substrates having different base sequence were compared for sensitivity. For the series of Substrates studied, sequence was found to significantly influence cleavage rate and ultimate sensitivity of the Assay. Sequence dependence for RNase T1 was pronounced with cleavage preference being 'gg'>'gc'>'ga'>'gu'. Of cleavable domains tested that contained a 'gg' dinucleotide, the triplet motif 'ggc' provided greater sensitivity than 'ggu'. Substrate SEQ ID NO:30 was most active with the RNase enzymes tested and was chosen as the preferred Substrate of the invention.

Results of Substrate activity testing using the visual detection methods for RNase A are summarized in Table 6 and for RNase T1 are summarized in Table 7. Of 28 Substrate ODNs tested, Substrate SEQ ID:30, having composition 5'-Fluorescein-AauggcA-QSY-7-3', was identified as having the most favorable properties and is offered as a preferred Substrate for use in the method of the invention.

TABLE 6

Sensitivity of Different Substrate ODNs to Ribonuclease A.

| | Concentration of RNase A | | |
|---|---|---|---|
| Substrate ODN | 1 ng/ml | 100 pg/ml | 10 pg/ml |
| SEQ ID NO:3 | ++ | + | − |
| SEQ ID NO:4 | − | − | − |
| SEQ ID NO:5 | ++ | + | − |
| SEQ ID NO:6 | − | − | − |
| SEQ ID NO:7 | + | − | − |
| SEQ ID NO:8 | +++ | +++ | + |
| SEQ ID NO:9 | − | − | − |
| SEQ ID NO:10 | ++ | − | − |
| SEQ ID NO:11 | ++ | − | − |
| SEQ ID NO:12 | ++ | − | − |
| SEQ ID NO:13 | ++ | + | − |
| SEQ ID NO:14 | ++ | + | − |
| SEQ ID NO:15 | +++ | + | − |
| SEQ ID NO:16 | +++ | ++ | − |
| SEQ ID NO:17 | +++ | + | − |

TABLE 6-continued

Sensitivity of Different Substrate ODNs to Ribonuclease A.

| | Concentration of RNase A | | |
|---|---|---|---|
| Substrate ODN | 1 ng/ml | 100 pg/ml | 10 pg/ml |
| SEQ ID NO:22 | +++ | ++ | − |
| SEQ ID NO:23 | +++ | + | − |
| SEQ ID NO:24 | +++ | + | − |
| SEQ ID NO:27 | +++ | ++ | + |
| SEQ ID NO:28 | +++ | ++ | + |
| SEQ ID NO:29 | +++ | +++ | + |
| SEQ ID NO:30 | +++ | +++ | ++ |

+++ = maximum intensity
++ = moderate intensity
+ = faint but above background
− = negative (identical to background)

Table 6: Sensitivity of different Substrate ODNs to Ribonuclease A. A series of Substrate ODNs were synthesized and tested for sensitivity to RNase A degradation. Stock enzyme was serial diluted to achieve final concentrations of 1 ng/ml, 100 pg/ml, and 10 pg/ml as indicated. Reactions were examined for fluorescence emission by visual inspection using an ultraviolet (UV) light source for excitation. Results were scored as +++, ++, +, or − based on relative signal intensity.

TABLE 7

Sensitivity of Different Substrate ODNs to Ribonuclease T1.

| | Concentration of RNase T1 | | |
|---|---|---|---|
| Substrate ODN | $10^{-3}$ units/ml | $10^{-4}$ units/ml | $10^{-5}$ units/ml |
| SEQ ID NO:3 | − | − | − |
| SEQ ID NO:4 | + | − | − |
| SEQ ID NO:5 | − | − | − |
| SEQ ID NO:6 | − | − | − |
| SEQ ID NO:7 | + | − | − |
| SEQ ID NO:8 | − | − | − |
| SEQ ID NO:9 | + | + | − |
| SEQ ID NO:10 | + | − | − |
| SEQ ID NO:11 | + | − | − |
| SEQ ID NO:12 | +++ | ++ | − |
| SEQ ID NO:13 | +++ | ++ | − |
| SEQ ID NO:14 | +++ | +++ | + |
| SEQ ID NO:15 | +++ | + | − |

TABLE 7-continued

Sensitivity of Different Substrate ODNs to Ribonuclease T1.

| Substrate ODN | Concentration of RNase T1 | | |
|---|---|---|---|
| | $10^{-3}$ units/ml | $10^{-4}$ units/ml | $10^{-5}$ units/ml |
| SEQ ID NO:16 | +++ | +++ | – |
| SEQ ID NO:17 | – | – | – |
| SEQ ID NO:22 | +++ | + | – |
| SEQ ID NO:23 | ++ | – | – |
| SEQ ID NO:24 | ++ | + | – |
| SEQ ID NO:27 | +++ | ++ | + |
| SEQ ID NO:28 | +++ | +++ | ++ |
| SEQ ID NO:29 | +++ | +++ | ++ |
| SEQ ID NO:30 | +++ | +++ | +++ |

+++ = maximum intensity
++ = moderate intensity
+ = faint but above background
– = negative (identical to background)

Table 7: Sensitivity of different Substrate ODNs to Ribonuclease T1. A series of Substrate ODNs were synthesized and tested for sensitivity to RNase T1 degradation. Stock enzyme was serial diluted to achieve final concentrations of 0.001 units/ml, 0.0001 units/ml, and 0.00001 units/ml as indicated. Reactions were examined for fluorescence emission by visual inspection using an ultraviolet (UV) light source for excitation. Results were scored as +++, ++, +, or – based on relative signal intensity.

12. EXAMPLE 7

Assay Sensitivity 12.1. Introduction

The preferred Substrate SEQ ID NO:30 was tested for sensitivity in detecting low levels of ribonuclease enzymes using the method of the invention. Both visual and fluorometric detection protocols were examined.

12.2. Materials and Reagents

Reagents used to conduct the nuclease degradation experiments of this Example include a Substrate oligonucleotide SEQ ID NO:30. Other equipment and reagents were similar to those used in prior Examples.

12.3. Sensitivity of the Visual Detection Method

It is commonly accepted that fluorometry provides for high sensitivity. To be useful, the visual method must also offer high sensitivity. Assays were conducted using the method of the invention with visual detection. Substrate SEQ ID NO:30 was mixed in 1× Assay Buffer at a concentration of 500 nM (50 pmoles ODN in 100 ul volume) in thin-walled, UV transparent tubes. Negative Control reactions did not receive nuclease. Dilutions of stock RNase A, RNase 1, and RNase T1 were made in water. Undiluted and diluted nuclease (1 ul) was added to respective 100 ul Assay Mixes resulting in final dilution factors of $10^{-2}$, $10^{-3}$, $10^{-4}$, $10^{-5}$, $10^{-6}$, and $10^{-7}$. Assays were incubated at room temperature for 10 minutes and visually examined for fluorescence emission with UV excitation. Results were recorded using digital photography and are shown in FIG. 7. The presence of RNase enzyme activity was clearly detectable by visual examination at all concentrations tested, demonstrating the utility of this assay format. The experiment took about 30 minutes to perform, including 15 minutes to set-up serial dilutions, 10 minutes incubation, and 5 minutes to visualize and photograph. Thus the method of the invention allows for a rapid, simple, and convenient visual assay for the presence of ribonuclease activity. Assay sensitivity was in the range needed for an RNase QC assay and, surprisingly, was comparable to that obtained using a fluorometer for detection, as outlined below.

12.4. Sensitivity of the Fluorometric Detection Methods

Assays were conducted using the method of the invention with fluorometric detection. Substrate SEQ ID NO:30 was mixed in 1× Assay Buffer at a concentration of 50 nM (50 pmoles ODN in 1.0 ml volume) in RNase-free disposable cuvettes. Negative Control reactions did not receive nuclease. Dilutions of stock RNase A, RNase 1, and RNase T1 were made in water. Undiluted and diluted nuclease (1 ul) was added to respective 1.0 ml Assay Mixes resulting in final dilution factors of $10^{-3}$, $10^{-4}$, $10^{-5}$, $10^{-6}$, $10^{-7}$, $10^{-8}$, and $10^{-9}$. Assays were incubated at 37° C. for 1 hour and examined for fluorescence emission at 520 nm using 490 nm excitation in a PTI fluorometer. Results are summarized below. Final enzyme concentration reported notes the lowest concentration tested that was reproducibly positive with a signal:noise ratio of at least 2:1.

TABLE 8

Sensitivity of the RNase Assay using Fluorometric Detection

| Nuclease | Dilution Factor | Enzyme Concentration |
|---|---|---|
| RNase A | $10^{-8}$ | 10 pg/ml |
| RNase T1 | $10^{-8}$ | 0.00001 units/ml |
| RNase 1 | $10^{-7}$ | 0.00001 units/ml |

Thus the fluorometric method of the invention allows for a highly sensitive assay for the presence of ribonuclease activity. If needed, sensitivity can be increased by extending incubation time.

13. EXAMPLE 8

Practical Laboratory Application of the Assay 13.1. Introduction

The method of the invention is intended for use as a QC assay to detect the presence of ribonuclease enzyme activity in laboratory reagents. Many commercial enzyme preparations are marketed as being "RNase Free". A series of enzymes from commercial sources were tested for ribonuclease activity using the preferred Substrate with the visual detection method to ascertain whether such claims were valid or if these commercial preparations were actually contaminated with detectable levels of ribonuclease activity.

13.2. Materials and Reagents

Reagents used to conduct the nuclease degradation experiments of this Example include Substrate oligonucleotide SEQ ID NO:30. Equipment and other reagents were similar to those used in earlier Examples.

13.3. Ribonuclease Assay on Commercial Enzyme Samples

Enzymes were obtained from New England Biolabs (NEB) or Ambion as indicated. Test sample (10 ul) was mixed with 1× buffer (90 ul) for a final volume of 100 ul with 50 pmoles of Substrate SEQ ID NO:30 in 0.5 ml RNase-free microtubes. Assay Mixes were incubated 60 minutes at 37° C. and visually examined under UV excitation for fluorescence emission. After scoring for results, 1 ul (1 ug) of RNase A was added to each tube. The Assay was incubated an additional 5 minutes at 37° C. and re-scored. The addition of RNase A represents a control for the absence of an Assay inhibitor and validates negative results. The "plus RNase A" control was omitted whenever the primary assay was already positive. Results are summarized in Table 9. Of the 23 laboratory reagents tested, one sample (DNA restriction endonuclease Xho I) was identified that was contaminated with RNase activity.

The Assay proved to be both rapid and easy to perform in this application. Further, a contaminated reagent was identified from a commercial source that, if used in an experiment involving RNA, could have resulted in a compromised experiment due to RNA degradation. Using the method of the invention, routine testing of laboratory reagents can easily be done to ensure that a suitable RNase-free environment is present whenever working with RNA.

TABLE 9

RNase Testing of Commercially Obtained Reagents.

| Enzyme | Source | Assay Results | +RNase A Control | Sold as being RNase-Free? |
|---|---|---|---|---|
| RNase A | Ambion | +++ | ND | No |
| RNase T1 | Ambion | +++ | ND | No |
| RNase 1 | Ambion | +++ | ND | No |
| Mung Bean Nuclease | Ambion | + | ND | No |
| S1 Nuclease | Ambion | +++ | ND | No |
| DNase I | Ambion | − | +++ | Yes |
| Super Taq | Ambion | − | +++ | Yes |
| T7 RNA Polymerase | Ambion | − | +++ | Yes |
| Klenow DNA Polymerase | Ambion | − | +++ | Yes |
| T4 DNA Ligase | Ambion | − | +++ | Yes |
| Proteinase K | Ambion | − | +++ | Yes |
| T4 Polynucleotide Kinase | Ambion | − | +++ | Yes |
| Nuclease free water | Ambion | − | +++ | Yes |
| Bam HI | NEB | − | +++ | Yes |
| Hind III | NEB | − | +++ | Yes |
| Kpn I | NEB | − | +++ | Yes |
| Msp I | NEB | − | +++ | Yes |
| Nco I | NEB | − | +++ | Yes |
| Nde I | NEB | − | +++ | Yes |
| Sac I | NEB | − | +++ | Yes |
| Sal I | NEB | − | +++ | Yes |
| Xba I | NEB | − | +++ | Yes |
| Xho I | NEB | +++ | ND | Yes |

+++ = maximum intensity
++ = moderate intensity
+ = faint but above background
− = negative (identical to background)

Table 9: RNase testing of commercially available reagents. A series of commercially available reagents were diluted 1:10 with Assay Buffer to a final volume of 100 ul. An RNase detection assay was performed using the method of the invention with Substrate oligonucleotide SEQ ID NO:30. Reactions were examined for fluorescence emission by visual inspection using an ultraviolet (UV) light source for excitation. Results were scored as +++, ++, +, or − based on relative signal intensity. As a control, RNase A (1 ug) was added to negative reactions and the Assay was re-scored. ND=not done.

14. REFERENCES

14.1. Literature Citations

Current Protocols in Molecular Biology, John Wiley & Sons, Inc.

Caruthers, M. H., Beaton, G., Wu, J. V., and Wiesler, W. (1992) Chemical synthesis of deoxyoligonucleotides and deoxyoligonucleotide analogs. Methods Enzymol., 211: 3-20.

Cummins, L. L., Owens, S. R., Risen, L. M., Lesnik-, E. A., Freier, S. M., McGee, D., Guinosso, C. J., and Cook, P. D. (1995) Characterization of fully 2'-modified oligoribonucleotide hetero- and homoduplex hybridization and nuclease sensitivity. Nucleic Acids Res., 23:2019-2024.

D'Alessio, G., and Riordan, J. F., Editors. Ribonucleases: structures and functions. (1997) Academic Press, New York.

Egly, J. M., and Kempf, J. (1976) Detection and estimation of very low ribonuclease activities in biological fluids. FEBS Letters, 63:250-254.

Ghosh, S. S., Eis, P. S., Blumeyer, K., Fearon, K., and Millar, D. P. (1994) Real time kinetics of restriction endonuclease cleavage monitored by fluorescence resonance energy transfer. Nucleic Acids Res., 22:3155-3159.

Greiner-Stoeffele, T., Grunow, M., and Hahn, U. (1996) A general ribonuclease assay using methylene blue. Anal. Biochem., 240:24-28.

Hanne, A., Ramanujam, M. V., Rucker, R., and Krupp, G. (1998) Fluorescence resonance energy transfer (FRET) to follow ribozyme reactions in real time. Nucleosides and Nucleotides, 17:1835-1850.

James, D. A., and Woolley, G. A. (1998) A fluorescence-based assay for ribonuclease A activity. Anal. Biochem., 264:26-33.

Karn, R. C., Crisp. M., Yount, E. A., and Hodes, M. E. (1979) A positive zymogram method for ribonuclease. Anal. Biochem., 96:464-468.

Karpetsky, T. P., Davies, G. E., Shriver, K. K., and Levy, C. C. (1980) Use of polynucleotide/polyacrylamide-gel electrophoresis as a sensitive technique for the detection and comparison of ribonuclease activities. Biochem. J., 189: 277-284.

Kelemen, B. R., Klink, T. A., Behlke, M. A., Eubanks, S. R., Leland, P. A., and Raines, R. T. (1999) Hypersensitive substrate for ribonucleases. Nucleic Acids Res., 27:3696-3701.

Kempe, T., Chow, F., Sundquist, W. I., Nardi, T. J., Paulson, B., and Peterson, S. M. (1982) Selective 2'-benzoylation at the cis 2'-3'-diols of protected ribonucleotides. New solid phase synthesis of RNA and DNA-RNA mixtures. Nucleic Acids Res., 10:6695-6714.

Kunitz, M. (1946) A spectrophotometric method for the measurement of ribonuclease activity. J. Biol. Chem., 164:563-568.

Morrison, L. E. (1992) Detection of energy transfer and fluorescence quenching. In: Nonisotopic DNA probe techniques, Larry J. Kricka, editor, pp. 311-352. Academic Press, Inc., New York.

Oshima, T., Uenishi, N., and Imahori, K. (1976) Simple assay methods for ribonuclease T1, T2, and nuclease P1. Anal. Biochem., 71:632-634.

Sambrook, J., Fritsch, E. F., and Maniatis, T. (1989) Molecular cloning: a laboratory manual, $2^{nd}$ edition. Cold Spring Harbor Laboratory Press, Cold Spring Harbor, N.Y.

Scaringe, S. A., Francklyn, C., and Usman, N. (1990) Chemical synthesis of biologically active oligoribonucleotides using beta-cyanoethyl protected ribonucleoside phosphoramidites. Nucleic Acids Res., 18:5433-5441.

Steyaert, J., Haikal, A. F., Wyns, L., and Stanssens, P. (1991a) Subsite interactions of ribonuclease T1: Asn36 and Asn98 accelerate GpN transesterification through interactions with the leaving nucleoside N. Biochemistry, 30:8666-8670.

Steyaert, J., Wyns, L., and Stanssens, P. (1991b) Subsite interactions of Ribonuclease T1: viscosity effects indicate that the rate-limiting step of GpN transesterification depends of the nature of N. Biochemistry, 30:8661-8665.

Wagner, A. P., Iordachel, M. C., and Wagner, L. P. (1983) A simple spectrophotometric method for the measurement of ribonuclease activity in biological fluids. J. Biochem. Biophys. Methods, 8:291-297.

Watanabe, H., Ando, E., Ohgi, K., and Irie, M. (1985) The subsite structures of guanine-specific ribonucleases and a guanine-preferential ribonuclease: cleavage of oligoinosinic acids and poly-I. J. Biochem., 98:1239-1245.

Wilson, C. W. (1969) A rapid staining technique for detection of RNase after polyacrylamide gel electrophoresis. Anal. Biochem., 31:506-511.

Wilson, G. M., Lu, H., Sun, H., Kennedy, A., and Brewer, G. (2000) A fluorescence-based assay for 3'_5' exoribonucleases: potential applications to the study of mRNA decay. RNA, 6:458-464.

Wincott, F., Direnzo, A., Shaffer, C., Grimm, S., Tracz, D., Workman, C., Sweedler, D., Gonzalez, C., Scaringe, S., Usman, N. (1995) Synthesis, deprotection, analysis and purification of RNA and ribozymes. Nucleic Acids Res., 23:2677-2684.

Witmer, M. R., Falcomer, C. M., Weiner, M. P., Kay, M. S., Begley, T. P., Ganem, B., and Scheraga, H. A. (1991) U-3'-BCIP: a chromogenic substrate for the detection of RNase A in recombinant DNA expression systems. Nucleic Acids Res., 19:1-4.

Yaron, A., Carmel, A., and Katchalski-Katzir, E. (1979) Intramolecularly quenched fluorogenic substrates for hydrolytic enzymes. Anal. Biochem., 95:228-235.

Zelenko, O., Neumann, U., Brill, W., Pieles, U., Moser, H. E., and Hofsteenge, J. (1994) A novel fluorogenic substrate for ribonucleases: synthesis and enzymatic characterization. Nucleic Acids Res., 22:2731-2739.

14.2. Patent Citations

Burke, T. J., Bolger, R. E., Checovich, W. J., and Tompson, D. V. (1998) Method and kit for detecting nucleic acid cleavage utilizing a covalently attached fluorescent tag. U.S. Pat. No. 5,786,139.

Duck, P., Bender, R., Crosby, W., and Robertson, J. G. (1989) Nucleic acid compositions with scissile linkage useful for detecting nucleic acid sequences. U.S. Pat. No. 4,876,187.

Gelfand, D. H., Holland, P. M., Saiki, R. K., and Watson, R. M. (1993) Homogenous assay using the nuclease activity of a nucleic acid polymerase. U.S. Pat. No. 5,210,015.

Livak, K. J., Flood, S. J. A., Marmaro, J., and Mullah, K. B. (1999) Hybridization assay using self-quenching fluorescence probe. U.S. Pat. No. 5,876,930.

Maggio, E. T., (11980) Chemically induced fluorescence immunoassay. U.S. Pat. No. 4,220,450.

Nadeau, J. G., Pitner, B., Linn, C. P., and Schram, J. L. (1999) Detection of nucleic acids by fluorescence quenching. U.S. Pat. No. 5,958,700.

Nazarenko, I. A., Bhatnagar, S. K., Winn-Deen, E. S., and Hohman, R. J. (1999) Nucleic acid amplification oligonucleotides with molecular energy transfer labels and methods based thereon. U.S. Pat. No. 5,866,336.

Tyagi, S., Kramer, F. R., and Lizardi, P. M. (11999) Detectably labeled dual conformation oligonucleotide probes, assays and kits. U.S. Pat. No. 5,925,517.

14.3. Commercial Catalog Citations

Pan Vera Corporation
Catalog (2000), Section 3.10.
545 Science Drive, Madison, Wis. 53711.
Ambion, Inc.
Catalog (1999), p104.
2130 Woodward Street, Austin, Tex. 78744.
Mo Bio Laboratories, Inc.
Web Catalog (2000), http://www.mobio.com/
Solana Beach, Calif. 92075

All publications, patents and patent applications mentioned in this specification are herein incorporated by reference into the specification to the same extent as if each individual publication, patent or patent application was specifically and individually indicated to be incorporated herein by reference.

What is claimed is:

1. A nucleic acid, comprising:

(a) an enzymatic cleavage domain comprising a formula: $5'-N_1-n-N_2-3'$, wherein:

(i) "$N_1$" represents zero to five 2'-modified ribonucleotide residues:

(ii) "$N_2$" represents one to five 2'-modified ribonucleotide residues; and (iii) "n" comprises the sequence "auggc";

(b) a fluorescence reporter group on one side of an internucleotide linkage; and (c) a non-fluorescent fluorescence-ciuenching group on a side of the internucleotide linkage opposite the fluorescence reporter group.

2. The nucleic acid of claim 1, wherein $N_1$ and $N_2$ each represent one 2'-modified ribonucleotide residue.

3. The nucleic acid of claim 2, wherein the 2'-modified ribonucleotide residue is an adenosine.

* * * * *